US008754040B2

(12) United States Patent
Sekimizu et al.

(10) Patent No.: US 8,754,040 B2
(45) Date of Patent: Jun. 17, 2014

(54) CYCLIC PEPTIDE COMPOUND, METHOD FOR PRODUCING SAME, ANTI-INFECTIVE AGENT, ANTIBIOTIC-CONTAINING FRACTION, ANTIBIOTIC, METHOD FOR PRODUCING ANTIBIOTIC, ANTIBIOTIC-PRODUCING MICROORGANISM, AND ANTIBIOTIC PRODUCED BY SAME

(75) Inventors: Kazuhisa Sekimizu, Tokyo (JP); Hiroshi Hamamoto, Tokyo (JP); Kazuhisa Murakami, Osaka (JP)

(73) Assignees: Genome Pharmaceuticals Institute Co., Ltd., Tokyo (JP); The University of Tokyo, Tokyo (JP)

(*) Notice: Subject to any disclaimer, the term of this patent is extended or adjusted under 35 U.S.C. 154(b) by 0 days.

(21) Appl. No.: 13/699,161

(22) PCT Filed: May 25, 2011

(86) PCT No.: PCT/JP2011/061928
§ 371 (c)(1),
(2), (4) Date: Nov. 20, 2012

(87) PCT Pub. No.: WO2011/148959
PCT Pub. Date: Dec. 1, 2011

(65) Prior Publication Data
US 2013/0203654 A1 Aug. 8, 2013

(30) Foreign Application Priority Data

May 25, 2010 (JP) .................. 2010-119138
May 25, 2010 (JP) .................. 2010-119139
May 25, 2010 (JP) .................. 2010-119140

(51) Int. Cl.
*A01N 37/18* (2006.01)
*A61K 38/04* (2006.01)
*C07K 7/06* (2006.01)

(52) U.S. Cl.
CPC ...................... *C07K 7/06* (2013.01)
USPC ........................................ 514/2.7

(58) Field of Classification Search
CPC ........................................ C07K 7/06
See application file for complete search history.

(56) References Cited

U.S. PATENT DOCUMENTS

2008/0070884 A1* 3/2008 Von Nussbaum et al. .... 514/183

FOREIGN PATENT DOCUMENTS

| JP | 06-099444 A | 4/1994 |
|---|---|---|
| JP | 3339235 B2 | 10/2002 |
| JP | 2003-113192 A | 4/2003 |
| JP | 2007-131552 A | 5/2007 |
| JP | 2007-327964 A | 12/2007 |
| JP | 4054576 B2 | 2/2008 |
| JP | 4057426 B2 | 3/2008 |
| JP | 2008-518986 A | 6/2008 |
| WO | 01-86287 A1 | 11/2001 |

OTHER PUBLICATIONS

International Search Report of PCT/JP2011/061928, mailing date of Jul. 5, 2011.
Hamamoto, Hiroshi et al., "Kaiko Kansen Model o Riyo shi, Chiryo koka o shihyo to shita Shinkii Kokin'yaku Tansakuho no Kakuritsu", 2009 Antibiotics & Chemotherapy, vol. 25, No. 10, pp. 2134 to 2140.
Sekimizu Kazuhisa, "Model kaiko o Mochiita Yukosei Screening", 2007, Kagaku to Yakugaku no kyoshitsu, No. 157, pp. 10 to 22.

\* cited by examiner

*Primary Examiner* — Marcela M Cordero Garcia
*Assistant Examiner* — Kaipeen Yang
(74) *Attorney, Agent, or Firm* — Westerman, Hattori, Daniels & Adrian, LLP

(57) ABSTRACT

Provided are: a novel compound having a structure different from that of existing drugs; a novel microorganism capable of producing the novel compound; and further; a novel compound effective to a multiple-drug-resistant bacterium. To provide a novel compound having a high therapeutic effect which can be expected to have a low hurdle for practical realization by selecting an intended compound from many candidate compounds based not only on an antibacterial activity but also on evaluation including a therapeutic effect, a cyclic peptide compound shown by the following formula (1) or a pharmaceutically allowable salt thereof and a microorganism with Accession No. NITE BP-870 or a microorganism mutated naturally or artificially therefrom are provided.

(1)

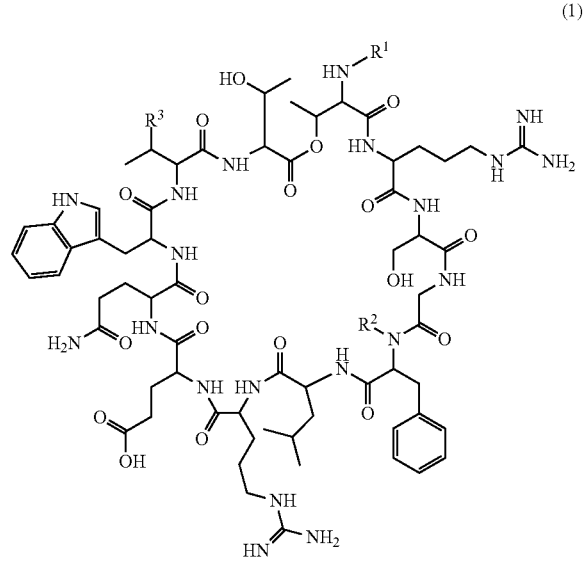

(In the formula (1), $R^1$ represents an acyl group having 7, 8, or 9 carbon atoms and optionally containing a substituent group; $R^2$ represents a methyl group or a hydrogen atom; and $R^3$ represents an ethyl group or a methyl group.)

27 Claims, 11 Drawing Sheets

P1

P2

SEQUENCE LISTING

```
<160> NUMBER OF SEQ ID NOS: 1

<210> SEQ ID NO 1
<211> LENGTH: 1507
<212> TYPE: DNA
<213> ORGANISM: Lysobacter
<220> FEATURE:
<223> OTHER INFORMATION: Almost entire length of amplified 16S rRNA of
      unknown strain belonging to genus Lysobacter

<400> SEQUENCE: 1
ttgagtttga tcctggctca gagtgaacgc tggcggcagg cctaacacat gcaagtcgaa      60
cggcagcaca gaggagcttg ctccttgggt ggcgagtggc ggacgggtga ggaatacgtc     120
ggaatctgcc tatttgtggg ggataacgta gggaaactta cgctaatacc gcatacgacc     180
tacgggtgaa agtgggggac cgcaaggcct cacgcagata gatgagccga cgtcggatta     240
gctagttggc ggggtaaagg cccaccaagg cgacgatccg tagctggtct gagaggatga     300
tcagccacac tggaactgag acacggtcca gactcctacg ggaggcagca gtggggaata     360
```

```
ttggacaatg ggcgcaagcc tgatccagcc atgccgcgtg tgtgaagaag gccttcgggt    420
tgtaaagcac ttttgtccgg aaagaaaagc tcagggttaa taaccatgag tcatgacggt    480
accggaagaa taagcaccgg ctaacttcgt gccagcagcc gcggtaatac gaagggtgca    540
agcgttactc ggaattactg ggcgtaaagc gtgcgtaggt ggtttgttaa gtctgatgtg    600
aaagccctgg gctcaacctg ggaatggcat tggaaactgg cttactagag tgcggtagag    660
ggtagcggaa ttcccggtgt agcagtgaaa tgcgtagata tcgggaggaa catccgtggc    720
gaaggcggct acctggacca gcactgacac tgaggcacga aagcgtgggg agcaaacagg    780
attagatacc ctggtagtcc acgccctaaa cgatgcgaac tggatgttgg gggcaacttg    840
gccctcagta tcgaagctaa cgcgttaagt tcgccgcctg ggaagtacgg tcgcaagact    900
gaaactcaaa ggaattgacg ggggcccgca caagcggtgg agtatgtggt ttaattcgat    960
gcaacgcgca gaaccttacc tggccttgac atgtcgagaa cttggcagag atgccttggt   1020
gccttcggga actcgaacac aggtgctgca tggctgtcgt cagctcgtgt cgtgagatgt   1080
tgggttaagt cccgcaacga gcgcaaccct tgtccttagt tgccagcacg taatggtggg   1140
aactctaagg agaccgccgg tgacaaaccg gaggaaggtg gggatgacgt caagtcatca   1200
tggcccttac ggccagggct acacacgtac tacaatggta gggacagagg gctgcaaacc   1260
cgcgagggta agccaatccc agaaacccta tctcagtccg gattggagtc tgcaactcga   1320
ctccatgaag tcggaatcgc tagtaatcgc agatcagcat tgctgcggtg aatacgttcc   1380
cgggccttgt acacaccgcc cgtcacacca tgggagtttg ttgcaccaga agcaggtagc   1440
ttaaccttcg ggagggcgct tgccacggtg tggccgatga ctggggtgaa gtcgtaacaa   1500
ggtagcc                                                             1507
```

CYCLIC PEPTIDE COMPOUND, METHOD FOR PRODUCING SAME, ANTI-INFECTIVE AGENT, ANTIBIOTIC-CONTAINING FRACTION, ANTIBIOTIC, METHOD FOR PRODUCING ANTIBIOTIC, ANTIBIOTIC-PRODUCING MICROORGANISM, AND ANTIBIOTIC PRODUCED BY SAME

TECHNICAL FIELD

The present invention relates to: a compound having a novel chemical structure; a method for manufacturing the said compound; an anti-infective therapeutic drug containing the said compound; and a novel microorganism which produces the said compound.

In addition, the present invention relates to: a fraction which contains an antibiotic substance fractionated from a culture produced from a novel microorganism belonging to a genus *Lysobacter*; a method for producing the said antibiotic substance; an antibiotic substance obtained by the said method; and further, use methods and production methods of an antibiotic substance showing an antibacterial activity while not showing a therapeutic effect and of an antibiotic substance showing both an antibacterial activity and a therapeutic effect, wherein these antibiotic substances are obtained from the said fraction.

Still in addition, the present invention relates to: a microorganism which produces an antibiotic substance; a method for manufacturing a novel antibiotic substance by culturing the said microorganism; and the said novel antibiotic substance.

BACKGROUND ART

An antibiotic substance is indispensable to control a microorganism and to cure an infective disease. However, excessive use of an antibiotic substance produces a resistant bacterium thereto, resulting in producing a multiple-drug-resistant bacterium having resistances to many drugs; and thus, it becomes a serious clinical problem. Especially methicillin-resistant *Staphylococcus aureus* (hereinafter abbreviated as MRSA) appears often in a clinical site, and thus, it became a social problem. Furthermore, *Enterococcus* having a resistance to vancomycin which is often used as a final therapeutic drug to MRSA (hereinafter the said vancomycin-resistant *Enterococcus* is abbreviated as VRE) has been separated from a clinical site in this country; and thus, a new therapeutic drug for a multiple-drug-resistant bacterium is eagerly wanted.

Especially, emergence of VRE which shows a resistance to vancomycin, the effective drug for MRSA, is considered to be a serious problem. This is assumed because *Enterococcus* itself resides always in the intestinal tract so that a potential carrier of the bacterium may be generated readily whereby a resistance gene thereof is transmitted to other bacterium due to long time residence in a patient body, and this in turn leading to increase of a risk to generate vancomycin-resistant *Staphylococcus aureus* (VRSA) and so on.

Separately from the problem of emergence of a resistant bacterium, an antibiotic substance having substantially high therapeutic effect while having higher safety than vancomycin and so on is eagerly wanted; and thus, an investigation is progressing to obtain a novel antibiotic substance not only being effective to MRSA and VRE but also having higher safety with less side effects and so on as compared with existing drugs.

As to the new therapeutic drug like this, linezolid, a synthetic antibiotic substance obtained by a total chemical synthesis method has been known. In addition, many investigations to find out an antibiotic substance showing effectiveness to the foregoing multiple-drug-resistant bacteria from antibiotic substances which are produced by various microorganisms have been carried out (Patent Documents 1 to 3). Among these Documents, in Patent Documents 1 and 2, a microorganism belonging to a genus *Lysobacter* which produces an antibiotic substance showing effectiveness to the foregoing multiple-drug-resistant bacterium and a method for producing the antibiotic substance by using this microorganism are described.

To achieve the foregoing object, not only creation of an antibiotic substance having a novel chemical structure and synthetic exploration of betterment and so on of existing antibiotic substances but also exploration of a novel microorganism capable of producing a useful and novel antibiotic substance which has not been reported before is being carried out widely. This is because an antibiotic substance produced by a microorganism is a natural substance produced in a living body, so that the substance is assumed much safer to a living body as compared with a chemically synthesized substance.

As to the microorganism which produces a novel antibiotic substance, many kinds of microorganisms have already been reported; and the microorganism belonging to a genus *Lysobacter* of Xanthomonadaceae, which is used in the present invention, has been reported as such a microorganism in Patent Documents 1, 2, 5, and so on. Among those Documents, in Patent Documents 2 and 5, a microorganism which produces an antibiotic substance having an antibacterial activity to the foregoing multiple-drug-resistant bacteria and a method for producing the antibiotic substance by using the said microorganism are described.

To provide a novel antibiotic substance not only having an antibacterial activity to methicillin-resistant *Staphylococcus aureus* (hereinafter abbreviated as MRSA) and vancomycin-resistant *Enterococcus* (hereinafter abbreviated as VRE), which are especially problematic in clinical site among the multiple-drug-resistant bacteria, but also showing an excellent therapeutic effect is eagerly wanted. However, most of the antibiotic substances which so far have been reported effective to the multiple-drug-resistant bacteria are those showing an antibacterial activity only to MRSA; there are not so many reports about the antibiotic substance also showing an antibacterial activity to VRE at the same time. As to example of the antibiotic substance effective both MRSA and VRE, an antibiotic substance showing an in vitro antibacterial activity to both the foregoing multiple-drug-resistant bacteria (hereinafter, antibacterial activity means "antibacterial activity shown in vitro" unless otherwise noted) is described among the antibiotic substances reported in Patent Document 3.

In addition, a novel microorganism belonging to a genus *Lysobacter* and a novel antibiotic substance produced and manufactured therefrom are described in Patent Documents 1 and 2; a novel microorganism belonging to a genus *Flavobac-*

*terium* and a novel antibiotic substance produced and manufactured therefrom are described in Patent Document 6; and a novel microorganism belonging to a genus *Streptomyces* and a novel antibiotic substance produced and manufactured therefrom are described in Patent Document 7.

On the other hand, inventors of the present invention constructed the "silkworm *Staphylococcus aureus* infection model" (Patent Document 4) by using, as an experimental animal, a silkworm (a larva of *Bombyx mori*), wherein the model was effectively used to explore an antibiotic substance; and then he carried out investigation on it.

Patent Document 1: Japanese Patent No. 3339235
Patent Document 2: Japanese Patent No. 4054576
Patent Document 3: Japanese Patent No. 4057426
Patent Document 4: Japanese Patent Laid-Open Publication No. 2007-327964
Patent Document 5: Japanese Examined Patent Application Publication No. H06-99444
Patent Document 6: Japanese Patent Laid-Open Publication No. 2003-113192
Patent Document 7: Japanese Patent Laid-Open Publication No. 2007-131552

DISCLOSURE OF INVENTION

Problems to be Solved by the Invention

In Patent Documents 2 ands 3, an antibiotic substance showing effectiveness not only to MRSA but also to VRE is described. However, in many previous reports, only effectiveness to MRSA has been described as reported in Patent Document 1; and thus, current situation is that there is almost no report about an antibiotic substance showing effectiveness to VRE. Accordingly, in view of possible emergence of a resistant bactrium, it is necessary to increase options of an antibiotic substance having following characterisitics: showing effectiveness not only to MRSA but also to VRE; having a chemical structure different from those of existing antibiotic substances shown in Patent Document 2, Patent Document 3, and so forth; and expecting to have an action mechanism to a resistant bacterium different from those of existing therapeutic drugs.

In addition, in most of previously reported examples, an antibiotic substance is selected mainly based on the in vitro antibactrium activity evaluated with the minimum inhibitory concentration (hereinafter, sometimes abbreviated as "MIC"); but because there is almost no example in which an antibiotic substance is selected by evaluation including an in vivo therapeutic effect, there remains final sifting of a therapeutic effect so that there is a problem of high hurdle for practical realization thereof.

As discussed above, a first problem to be solved by the present invention is to provide a novel compound having a chemical structure different from that of previous drugs, and in addition, to provide a novel compound which is also effective to a multiple-drug-resistant bacterium.

In addition, the object thereof includes to provide "a novel compound having a high therapeutic effect" which has already had a hurdle for practical realization lowered by selecting an intended compound from many candidate compounds based not only on an antibacterial activity but also on evaluation including a therapeutic effect.

In addition, as mentioned above, there are many antibiotic substances targeted to a multiple-drug-resistant bacterium, but there are not so many antibiotic substances clearly showing effectiveness to VRE, the practically realized antibiotic substance known to be effective to VRE being barely linezolid, which is an oxazolidinone-based antibiotic substance. However, linezolid is a synthetic antibiotic substance created by total chemical synthesis; and in view of a problem of safety to a living body and possible emergence of a resistant bacterium to an existing drug, there has been a need to further increase options of the antibiotic substance which is useful for a multiple-drug-resistant bacterium effective to VRE.

On the other hand, if an antibiotic substance showing effectiveness to VRE can be obtained from a substance produced from a microorganism, there is high possibility to lower a hurdle necessary to develop and manufacture a drug as compared with a compound by a total chemical synthesis method. This is because at least manufacturing thereof can be done by culturing, suggesting that manufactuing thereof may be done with lower cost and higher safety as comapared with a chemical synthesis method which requires chemicals such as a special catalyst and high temperature and high pressure.

As to the antibiotic substance which is produced by a microorganism and shows effectiveness to VRE as mentioned above, an antibiotic substance showing an antibacterial activity to both MRSA and VRE is described among antibiotic substances disclosed in the foregoing Patent Document 2. However, there has been no description yet about whether it shows an in vivo therapeutic effect to an infective disease or not (hereinafter, the term "therapeutic effect" is used to mean therapeutic effect to an infective disease confirmed with an in vivo evaluation system unless otherwise noted). This is because a therapeutic effectiveness of an antibiotic substance has been evaluated by assuming that magnitude of an antibacterial activity evaluated by the minimum inhibitory concentration (hereinafter, sometimes abbreviated as "MIC") reflects magnitude of a therapeutic effect of this antibiotic substance. This is presumably because there is no choice but to depend on MIC since there has been no convenient method to evaluate "therapeutic effect". However, by investigation of the present inventors as mentioned later, it was confirmed that "magnitude of an antibacterial activity" of an antibiotic substance evaluated by MIC does not necessarily reflect "magnitude of a therapeutic effect" of the said antibiotic substance.

In other words, almost all of the antibiotic substances previously reported were selected by evaluation of an antibacterial activity based on MIC whereby disclosing only "magnitude of antibacterial activity" without disclosing "magnitude of a therapeutic effect" yet.

Accordingly, to provide a fraction containing an antibiotic substance produced by a microorganism (hereinafter this is described as "antibiotic-substance-containing fraction") and an antibiotic substance obtained from the said fraction, it is important to select them by evaluating not only their shown antibacterial activities but also their therapeutic effects; and thus, a problem to be solved by the present invention is to provide an antibiotic-substance-containing fraction having high usefulness not known before which is selected as mentioned above and an antibiotic substance obtained from this fraction.

Then, inventors of the present invention thought that, by solving the foregoing problem, not only an antibiotic-substance-containing fraction and an antibiotic substance obtained therefrom which show both antibacterial activity and therapeutic effect may be selected, but also an antibiotic-substance-containing fraction and an antibiotic substance which show an antibacterial activity but do not show a therapeutic effect may be selected. Further, the inventors thought that, even though it is natural that the former is highly effective as a therapeutic drug for an infective disease, the antibiotic-substance-containing fraction and so on of the latter which have not attracted an attention before have properties suitably used as a microbial protection agent because they are not used as a therapeutic drug when used as a microbial protection agent so that substantially there is no need to consider emergence of a multiple-drug-resistant bacterium.

Namely, a second problem to be solved by the present invention is to provide: a fraction containing an antibiotic substance which is produced by an microorganism and has an effectiveness not known before; an antibiotic substance obtained therefrom; a manufacturing process thereof; and further, an antibiotic-substance-containing fraction and an antibiotic substance which are selected by evaluating the antibiotic-substance-containing fraction and the antibiotic substance based on not only an antibacterial activity but also whether or not a therapeutic effect exists. In addition, the object thereof includes to provide an antibiotic-substance-containing fraction and an antibiotic substance which show a therapeutic effect to a multiple-drug-resistant bacterium. Further in addition, the object thereof includes to provide a microbial protection agent which contains the antibiotic-substance-containing fraction or the antibiotic substance as mentioned above.

On the other hand, it is expected that an antibiotic substance obtained from substances produced from a microorganism has higher safety to a living body as compared with a synthetic substance, suggesting that an antibiotic substance like this can decrease development steps to make it a medical drug. For example, the manufacturing process mentioned above has a merit in that raw materials which are more benign to a living body than those of a chemical synthesis process may be used, and in addition, a more convenient and safer process and equipment may be used therein because manufacturing conditions of nearly ambient temperature and pressure can be used. Accordingly, this has a higher potential to decrease development steps to a medical drug as compared with an antibiotic substance created by a chemical synthesis.

However, as to the microorganism which produces an antibiotic substance showing not only effectiveness to MRSA but also antibacterial activity to VRE, a further investigation was necessary in view such matters as a therapeutic effect in a practical clinical site and emergence of a resistant bacterium, even though there is an example as described in Patent Document 2. In other words, there has been a desire: to find out a microorganism having characteristics to produce an antibiotic substance having an antibacterial activity not only to MRSA but also to VRE and actually showing a therapeutic effect; and to provide a novel antibiotic substance showing effectiveness to both MRSA and VRE by using this microorganism and a method for manufacturing the same.

In addition, in order to widely obtain a novel antibiotic substance regardless whether or not an antibacterial activity exists to MRSA, VRE, and so on, there has been a desire to provide a novel microorganism.

The present invention was made in view of the situation mentioned above; and thus, a third problem to be solved by the present invention is to provide a novel microorganism which can produce an antibiotic substance and to provide a novel microorganism which can be used in a method to manufacture an antibiotic substance; especially to provide a novel microorganism capable of producing a novel antibiotic substance which is effective to multiple-drug-resistant bactera, at least to both MRSA and VRE.

Means for Solving the Problems

In view of the situation mentioned above, in order to obtain a novel microorganism capable of producing an antibiotic substance, an antibiotic-substance-containing fraction obtained from this microorganism, and an antibiotic substance obtained therefrom, inventors of the present invention carried out an investigation on a method to evaluate the antibiotic-substance-containing fraction obtained from a culture supernatant of the said microorganism and the antibiotic substance obtained from this fraction by separation and purification treatments. As a result, when selecting a microorganism and a method for separation and purification of an antibiotic substance contained in a culture supernatant, inventors of the present invention thought of evaluation by MIC to *Staphylococcus aureus* as to an antibacterial activity of each sample with concurrent evaluation as to a therapeutic effect thereof. And then, investigation to obtain an intended microorganism strain and the antibiotic-substance-containing fraction having a high effectiveness as mentioned above was carried out by using, as the method to evaluate magnitude of a therapeutic effect of each sample, "the silkworm *Staphylococcus aureus* infection model" mentioned in Patent Document 4, which uses, as an experimental animal, a silkworm.

As a result, out of 14346 strains of soil bacteria separated from the soils taken from various parts of this nation, 3487 stains were found to show an antibacterial activity to *Staphylococcus aureus* in a culture supernatant thereof; and when a therapeutic effect of the culture supernatant of these bacteria was studied by the foregoing silkworm *Staphylococcus aureus* infection model, number of the microorganisms showing a therapeutic effect was decreased to 45 strains. From this result, it was confirmed that the antibacterial activity evaluated by MIC does not necessarily guarantee "therapeutic effect" of the evaluated antibiotic substance to an infective disease imposed by the MIC-related bacteria.

Then, when antibacterial spectra of the antibiotic-substance-containing fraction obtained from a culture supernatant of the forgoing 45 strains were studied, it was found that a microorganism showing an antibacterial activity to a multiple-drug-resistant bacterium of both MRSA and VRE was included in these 45 strains; and in addition, it was found that an antibiotic substance showing a therapeutic effect in the same level or higher as compared with vancomycin in the mouse *Staphylococcus aureus* infection model was included in the antibiotic-substance-containing fraction which was fractionated from a culture of the said microorganism. When the foregoing antibiotic substance which showed high therapeutic effect was studied in detail as to a chemical structure and so on, it was confirmed that this antibiotic substance was a novel antibiotic substance.

Further, when antibacterial spectra of other antibiotic-substance-containing fractions and antibiotic substances contained in the said fractions were studied, it became clear that the antibacterial spectra of the other antibiotic-substancecontaining fractions were the same as that of the said novel antibiotic substance, and that the chemical structure thereof was that of a related compound of the said novel antibiotic substance; and thus, it was confirmed that the fraction containing an antibiotic substance other than the said novel antibiotic substance in the final fractionation stage was also a highly effective fraction.

In addition, it was confirmed that the therapeutic effect ($ED_{50}$: amount of 50% effectiveness) shown in the fraction containing the said novel antibiotic substance was concentrated by 300-folds relative to that in the initially obtained fraction in its purification process, while the antibacterial activity thereof (MIC) was concentrated by only 5-folds.

This fact suggests that the antibiotic-substance-containing fraction in the early stage of purification process obtained by the fractionation procedure as mentioned later contains, with a high ratio, an antibiotic substance showing a comparatively high antibacterial activity but hardly showing a therapeutic effect. Accordingly, it was considered that these antibiotic substances contained in the antibiotic-substance-containing fraction in the early stage of purification process were difficult to be used as a therapeutic drug for an infective disease.

However, from the different point of view, to show high antibacterial activity while not showing a therapeutic effect may be inversely valuated as this to be suitable for an antibacterial agent such as a microbial protection agent because the antibiotic substance like this is not substantially used as a therapeutic drug for an infective disease. This is because this antibiotic substance is not used as a therapeutic drug so that there is no need to pay attention to emergence of a multiple-drug-resistant bacterium which is concerned when it is used as an antibacterial agent. In addition, this is removed from the fraction in the later stage of purification process, so that it was confirmed that there is no chemical structural resemblance to the foregoing novel antibiotic substance; and thus, there is no need, either, to pay attention to emergence of a multiple-drug-resistant bacterium by a cross-reaction with an antibiotic substance selected as a therapeutic drug for an infective disease.

In other words, the antibiotic-substance-containing fraction having a high antibacterial activity but a low therapeutic effect obtained from a fraction in the early stage of purification process and the antibiotic substance obtained therefrom are highly usable when they are used as a microbial protection agent.

In addition, it was found that the microorganism which produced the antibiotic-substance-containing fraction and the antibiotic substance showing an antibacterial activity to MRSA and VRE as mentioned above was a novel microorganism belonging to a genus *Lysobacter* (hereinafter, shown as "RH2180-5") from the results of the characteristic analysis thereof, analysis of the base sequence of 16S rRNA thereof and so on, and also from novelty and so on of the produced substance, and further it was found that the antibiotic-substance-containing fraction and the antibiotic substance obtained therefrom in the present invention were obtained from the novel microorganism; based on these findings, the present invention could be accomplished.

Further, when the antibiotic substance which showed a high therapeutic effect in the foregoing "mouse *Staphylococcus aureus* infection model" was studied in detail as to its chemical structure and so on, it was confirmed that this antibiotic substance is a cyclic peptide compound having a novel chemical structure. In addition, it was confirmed that, in addition to the substance mentioned above, cyclic peptide compounds related thereto having a similar chemical structure to the foregoing are contained in the culture supernatant and that these also show similar antibacterial spectra to that of the foregoing compound.

Namely, the present invention provides the following:

<1>

A cyclic peptide compound shown by the following formula (1) or a pharmaceutically allowable salt thereof.

[Chem. 1]

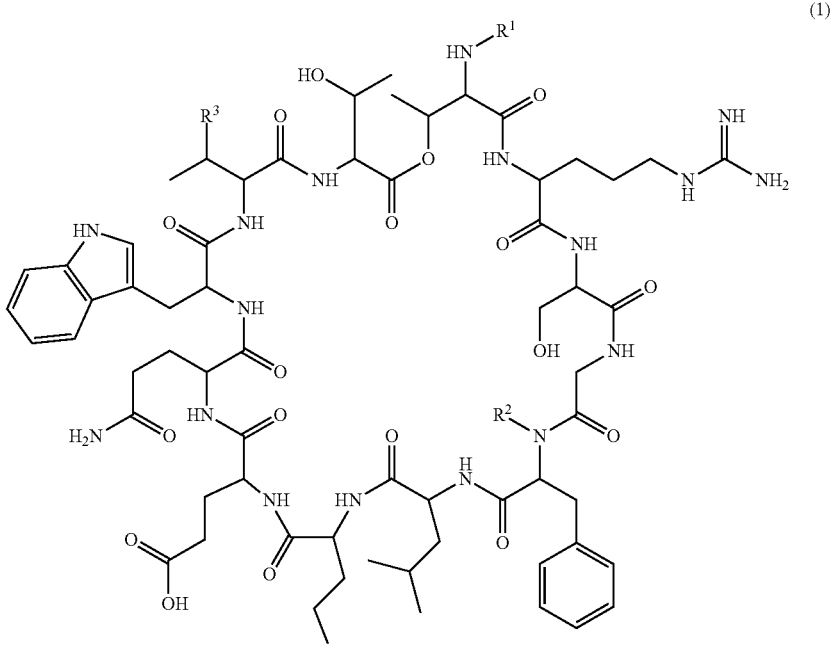

(1)

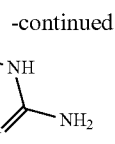
-continued (In the formula (1), R¹ represents an acyl group having 7, 8, or 9 carbon atoms and optionally containing a substituent group; R² represents a methyl group or a hydrogen atom; and R³ represents an ethyl group or a methyl group.)<

<2>

The cyclic peptide compound or the pharmaceutically allowable salt thereof according to <1>, wherein the substituent group of R¹ in the above formula (1) is a hydroxyl group.

<3>

The cyclic peptide compound or the pharmaceutically allowable salt thereof according to <1>, wherein R¹ in the above formula (1) is a 3-hydroxy-5-methyl-hexanoyl group, a 3-hydroxy-6-methyl-heptanoyl group, or a 3-hydroxy-7-methyl-octanoyl group.

<4>

The cyclic peptide compound or the pharmaceutically allowable salt thereof according to <1>, wherein, in the above formula (1), R¹ is a 3-hydroxy-5-methyl-hexanoyl group, R² is a methyl group, and R³ is an ethyl group.

<5>

The cyclic peptide compound or the pharmaceutically allowable salt thereof according to <1>, wherein, in the above formula (1), R¹ is a 3-hydroxy-7-methyl-octanoyl group, R² is a methyl group, and R³ is an ethyl group.

<6>

The cyclic peptide compound or the pharmaceutically allowable salt thereof according to any of <1> to <5>, wherein the cyclic peptide compound or the pharmaceutically allowable salt thereof is obtained from a culture that is produced by culturing of RH2180-5 strain, which belongs to a genus *Lysobacter* with Accession No. NITE BP-870 in NITE Patent Microorganisms Depositary (NPMD) of Incorporated Administrative Agency National Institute of Technology and Evaluation (NITE), or its mutant strain capable of producing a compound similar to the compound produced from the foregoing strain.

<7>

A method for manufacturing the cyclic peptide compound or the pharmaceutically allowable salt thereof according to any of <1> to <6>, characterized in that the cyclic peptide compound or the pharmaceutically allowable salt thereof is manufactured from a culture that is produced by culturing the RH2180-5 strain, which is capable of producing the cyclic peptide compound according to any of <1> to <6> and belongs to a genus *Lysobacter* with Accession No. NITE BP-870 in NITE Patent Microorganisms Depositary (NPMD) of Incorporated Administrative Agency National Institute of Technology and Evaluation (NITE), or its mutant strain capable of producing a compound similar to the compound produced from the foregoing strain.

<8>

A therapeutic drug for an infective disease, wherein the therapeutic drug contains the cyclic peptide compound or the pharmaceutically allowable salt thereof according to any of <1> to <6> together with a pharmaceutically allowable carrier.

<9>

An antibiotic-substance-containing fraction, characterized in that the antibiotic-substance-containing fraction is obtained by fractionating a culture which is produced by culturing a microorganism belonging to a genus *Lysobacter* with Accession No. NITE BP-870 and contains the cyclic peptide compound or the pharmaceutically allowable salt thereof according to any of <1> to <6>.

<10>

The antibiotic-substance-containing fraction according to <9>, wherein the antibiotic-substance-containing fraction is a fraction which contains an antibiotic substance showing an antibacterial activity.

<11>

The antibiotic-substance-containing fraction according to <9> or <10>, wherein the antibiotic-substance-containing fraction shows an antibacterial activity at least to both methicillin-resistant *Staphylococcus aureus* (MRSA) and vancomycin-resistant *Enterococcus* (VRE).

<12>

The antibiotic-substance-containing fraction according to any of <9> to <11>, wherein the antibiotic-substance-containing fraction is a fraction which contains an antibiotic substance showing a therapeutic effect to an infective disease at least due to *Staphylococcus aureus*.

<13>

The antibiotic-substance-containing fraction according to <12>, wherein the antibiotic-substance-containing fraction contains an antibiotic substance showing a therapeutic effect to an infective disease at least due to *Staphylococcus aureus* with the therapeutic effect thereof being the same or higher as compared with vancomycin.

<14>

The antibiotic-substance-containing fraction according to <9> or <10>, wherein the antibiotic-substance-containing fraction contains an antibiotic substance showing an antibacterial activity but not substantially showing a therapeutic effect.

<15>

The antibiotic-substance-containing fraction according to <14>, wherein the antibiotic substance showing an antibacterial activity but not substantially showing a therapeutic effect is used as a microbial protection agent.

<16>

A method for manufacturing an antibiotic substance, characterized in that any one of an antibiotic substance showing an antibacterial activity and an antibiotic substance showing a therapeutic effect to an infective disease or both is separated and purified from a culture which is produced by culturing a microorganism belonging to a genus *Lysobacter* with Accession No. NITE BP-870 and contains the cyclic peptide compound or the pharmaceutically allowable salt thereof according to any of <1> to <6>.

<17>

The method for manufacturing an antibiotic substance according to <16>, wherein the antibiotic substance shows an antibacterial activity at least to both methicillin-resistant *Staphylococcus aureus* (MRSA) and vancomycin-resistant *Enterococcus* (VRE).

<18>

The method for manufacturing an antibiotic substance according to <16> or <17>, wherein the antibiotic substance shows a therapeutic effect to an infective disease at least due to *Staphylococcus aureus*.

<19>

The method for manufacturing an antibiotic substance according to <16>, wherein the antibiotic substance is an antibiotic substance showing an antibacterial activity but not substantially showing a therapeutic effect.

<20>

An antibiotic substance, characterized in that the antibiotic substance is obtained from a culture which is produced by culturing a microorganism belonging to a genus *Lysobacter* with Accession No. NITE BP-870 and contains the cyclic peptide compound or the pharmaceutically allowable salt thereof according to any of <1> to <6>.

<21>

The antibiotic substance according to <20>, wherein the antibiotic substance shows an antibacterial activity at least to both methicillin-resistant *Staphylococcus aureus* (MRSA) and vancomycin-resistant *Enterococcus* (VRE).

<22>

The antibiotic substance according to <20> or <21>, wherein the antibiotic substance shows a therapeutic effect to an infective disease at least due to *Staphylococcus aureus*.

<23>

The antibiotic substance according to <22>, wherein the antibiotic substance shows a therapeutic effect to an infective disease at least due to *Staphylococcus aureus* with the therapeutic effect thereof being the same or higher as compared with vancomycin.

<24>

An antibiotic substance, characterized in that the antibiotic substance is obtained from a culture which is produced by culturing a microorganism belonging to a genus *Lysobacter* with Accession No. NITE BP-870 and contains the cyclic peptide compound or the pharmaceutically allowable salt thereof according to any of <1> to <6>, and that the antibiotic substance shows an antibacterial activity at least to both methicillin-resistant *Staphylococcus aureus* (MRSA) and vancomycin-resistant *Enterococcus* (VRE) while showing a therapeutic effect to an infective disease at least due to *Staphylococcus aureus*.

<25>

The antibiotic substance according to any of <20> to <24>, wherein the antibiotic substance is shown by the following formula (1).

[Chem. 2]

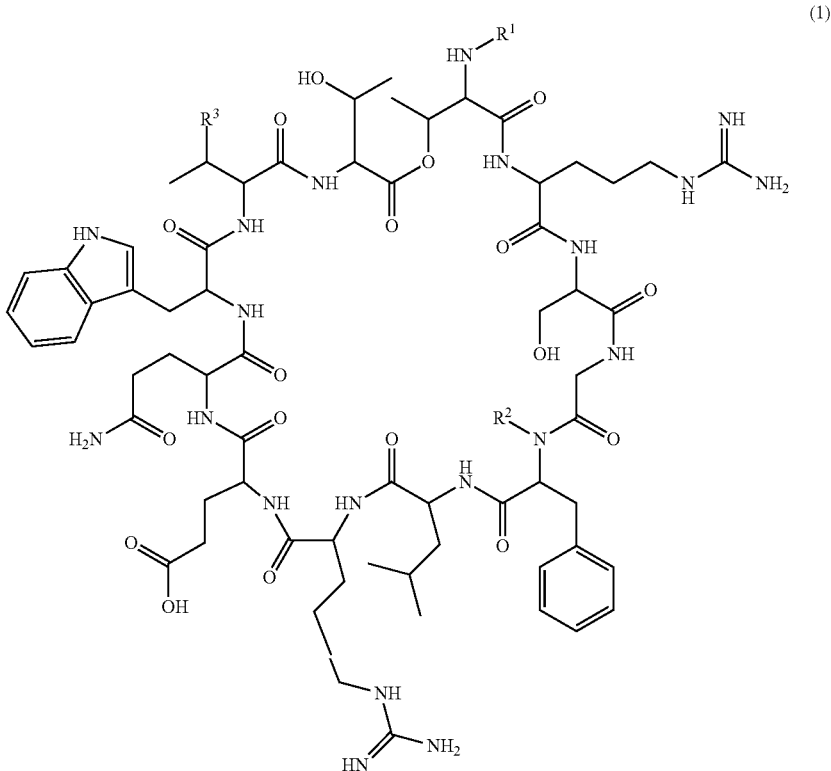

(1)

(In the formula (1), $R^1$ represents an acyl group having 7, 8, or 9 carbon atoms and containing one hydroxyl group; $R^2$ represents a methyl group or a hydrogen atom; and $R^3$ represents an ethyl group or a methyl group.)

<26>

A microbial protection agent, characterized in that the microbial protection agent contains the antibiotic-substance-containing fraction according to <9> or <10>.

<27>

A microbial protection agent, characterized in that the microbial protection agent contains the antibiotic substance according to <20>.

<28>

A microorganism, wherein the microorganism belongs to a genus *Lysobacter* with Accession No. NITE BP-870 or is a naturally or artificially mutated microorganism thereof, and is capable of producing a compound shown by the following formula (1) or a salt thereof.

[Chem. 3]

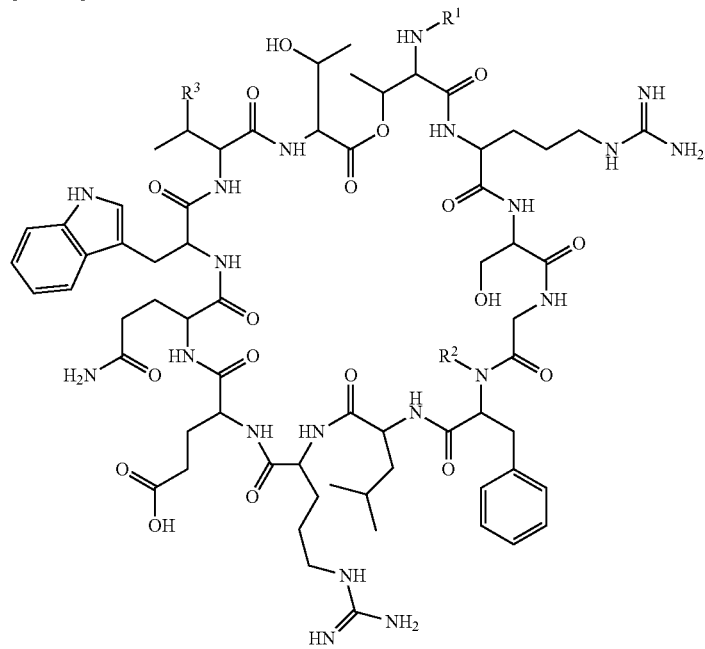

(1)

(In the formula (1), $R^1$ represents an acyl group having 7, 8, or 9 carbon atoms and containing one hydroxyl group; $R^2$ represents a methyl group or a hydrogen atom; and $R^3$ represents an ethyl group or a methyl group.)

<29>

The microorganism according to <28>, wherein the antibiotic substance has an antibacterial activity at least to methicillin-resistant *Staphylococcus aureus* (MRSA) and vancomycin-resistant *Enterococcus* (VRE).

<30>

The microorganism according to <28> or <29>, wherein the microorganism has the base sequence of the 16S rRNA region shown by the Sequence No. 1 in the sequence chart.

Advantages

According to the present invention, provided is a compound having a novel chemical structure which is effective to an infective disease and so on. In addition, provided are a compound having a novel chemical structure or a salt thereof which show effectiveness to many multiple-drug-resistant bacteria such as MRSA and VRE, a method for manufacturing them, and a novel microorganism which produces these compounds.

Further, according to the present invention, provided are a fraction containing a useful antibiotic substance produced from the novel microorganism and the antibiotic substance thereof. Among these antibiotic substances, there are some which show an antibacterial activity not only to MRSA but also to VRE, and there are some which show a high therapeutic effect to *Staphylococcus aureus*. Accordingly, the present invention has an effect to be able to provide a fraction containing an extremely useful, novel antibiotic substance and the novel antibiotic substance thereof.

Further, according to the present invention, provided is a novel microorganism capable of producing the foregoing antibiotic substances having an antibacterial activity. Especially, among the antibiotic substances produced by the microorganism of the present invention, there exists an antibiotic substance which is confirmed to have an antibacterial activity to MRSA and VRE with a high therapeutic effect; and thus, the present invention has an effect to be able to provide a novel microorganism capable of producing a novel antibiotic substance having a high effectiveness to a multiple-drug-resistant bacterium.

BRIEF DESCRIPTION OF DRAWINGS

FIG. 1 is a chart showing a fractionation result of the fraction which contains a substance showing a therapeutic effect obtained from a culture of RH2180-5 by using an ODS column. The vertical axis shows absorption strength, and the horizontal axis shows elution time (minutes). The numbers appeared above each of peak columns which are shown in separate frames show molecular weights of respective peak substances.

FIG. 2 shows the analysis result of amino acid composition of the RH2180-5 Peak 5 Substance.

FIG. 3 shows charts of analysis results of the RH2180-5 Peak 5 Substance by $^1$H-NMR and $^{13}$C-NMR. The vertical axis shows signal strength and the horizontal axis shows chemical shift (ppm).

FIG. 4 shows a chart of the MS-MS analysis result of the RH2180-5 Peak 5 Substance by TOF-MS (TOF: Time of Flight).

FIG. 5 shows charts of the MS-MS analysis results of the RH2180-5 Peak 1 substance and the RH2180-5 Peak 2 substance by TOF-MS (TOF: Time of Flight).

FIG. 6 shows charts of the MS-MS analysis results of the RH2180-5 Peak 3 substance and the RH2180-5 Peak 4 substance by TOF-MS (TOF: Time of Flight).

FIG. 7 shows charts of the MS-MS analysis results of the RH2180-5 Peak 6 substance and the RH2180-5 Peak 7 substance by TOF-MS (TOF: Time of Flight).

FIG. 8 shows charts of the MS-MS analysis results of the RH2180-5 Peak 8 substance and the RH2180-5 Peak 9 substance by TOF-MS (TOF: Time of Flight).

FIG. 9 shows a chemical structure of the RH2180-5 Peak 5 Substance obtained from the respective analysis results.

FIG. 10 shows a chemical structure of the RH2180-5 Peak 5 Substance obtained from the respective analysis results, with which three-dimensional conformations of amino acids are clearly shown.

FIG. 11 is a graph showing bacteriolytic activity of the RH-2180-5 Peak 5 Substance.

Figure 1:
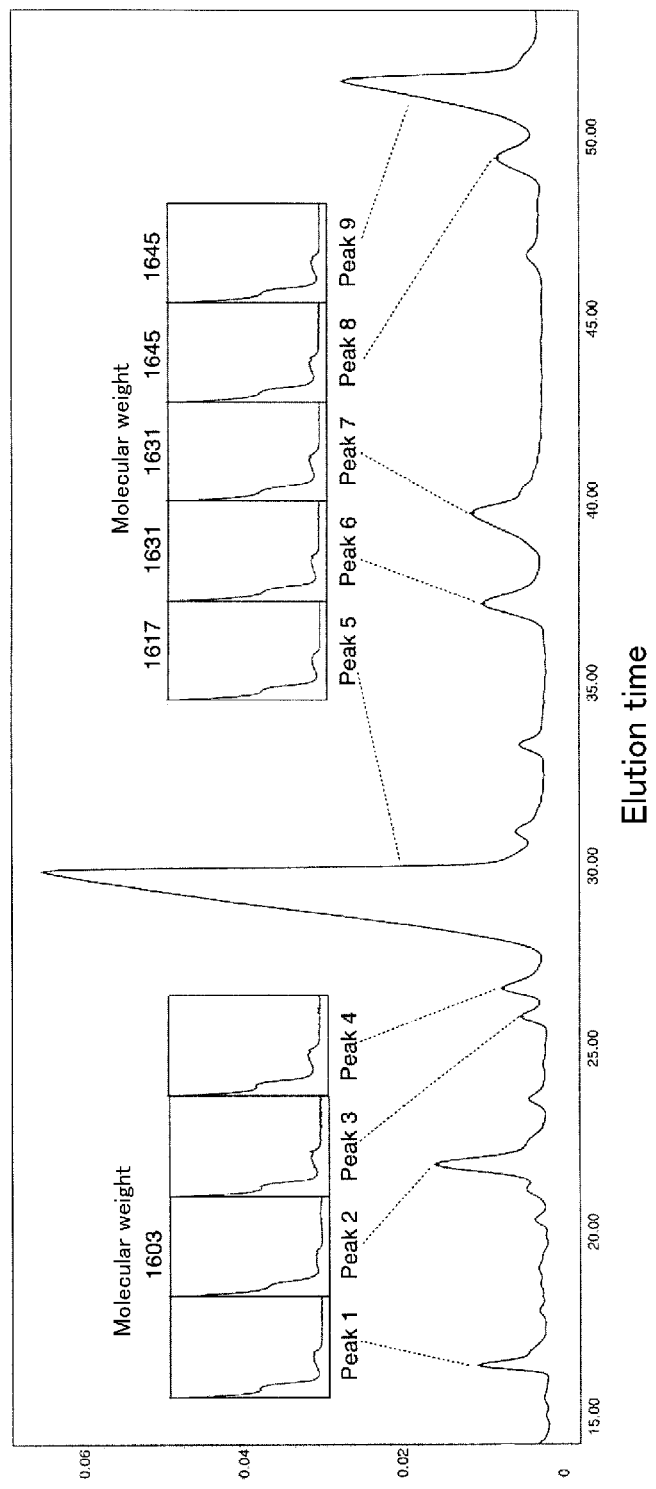
[FIG. 1]

eton of a 37-membered cyclic peptide structure, while a plurality of compounds with different groups of $R^1$ to $R^3$ have been confirmed. These have been isolated from a peak fraction separated by the final purification stage with RP-HPLC, which will be explained later, from a culture of a novel microorganism strain *Lysobacter* sp RH2180-5 which was found by inventors of the present invention and will be explained later; but a method to obtain "the cyclic peptide compound shown by the following formula (1) or the pharmaceutically allowable salt thereof" of the present invention is not limited to the foregoing method, so that they are independent of the method for manufacturing thereof and thus are not limited to those produced from a microorganism.

Meanwhile, each of the purified and isolated compounds is shown by the name of the microorganism strain attached with the peak name for short; namely, for example, the compound obtained from the Peak 1 has the name of "RH2180-5 Peak 1 Substance", or simply "P1".

[Chem. 4]

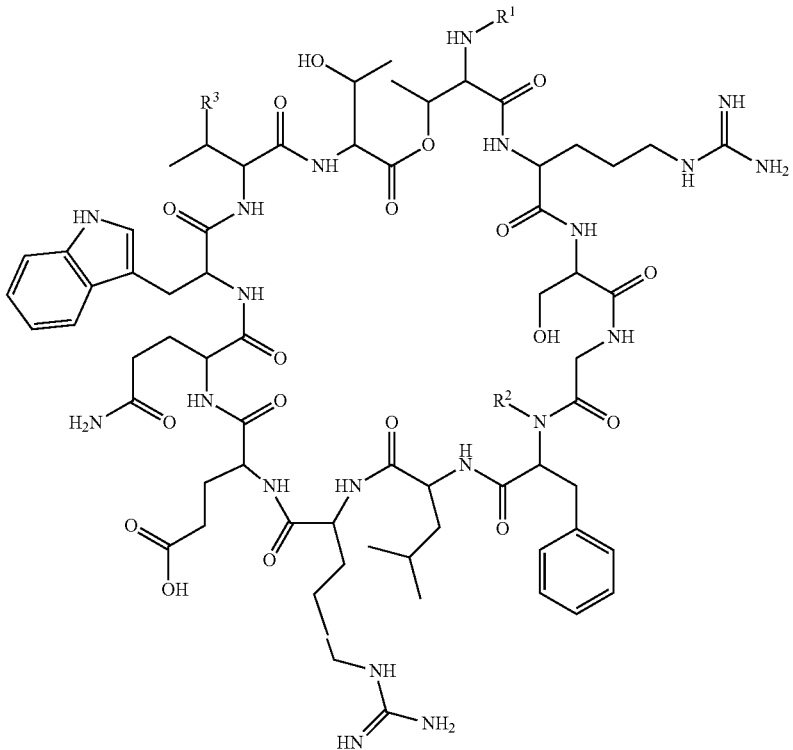

(1)

BEST MODES FOR CARRYING OUT THE INVENTION

Hereinafter, the present invention will be explained; but the present invention is not limited to specific embodiments described below and may be modified arbitrarily within its technical scope.

<Cyclic Peptide Compound of the Present Invention>

The present invention relates to a novel compound characterized by the following formula (1) which has a basic skel- (In the formula (1), $R^1$ represents an acyl group having 7, 8, or 9 carbon atoms and optionally containing a substituent group; $R^2$ represents a methyl group or a hydrogen atom; and $R^3$ represents an ethyl group or a methyl group.)

In the above formula (1), $R^1$ represents an acyl group having 7, 8, or 9 carbon atoms and optionally containing a substituent group. Number of the carbon atoms in the acyl group includes number of the carbon atom in [C=O] (one carbon atom). "Acyl group having 7, 8, or 9 carbon atoms" excluding the substituent group is shown by "R'—C(=O)—", wherein R' represents an alkyl group having 6, 7, or 8 carbon atoms. R' may be linear or branched, but preferably branched. Branched part is preferably a methyl group; and it is particularly preferable that the terminal opposite to [C=O] of R' be [CH$_3$(CH$_3$)CH-], though not particularly restricted. When R', namely R$^1$, is branched, number of the carbon atoms in the foregoing R$^1$ (7, 8, or 9) includes number of the carbon atoms in the branched part. Meanwhile, the substituent group of R$^1$ in the above formula (1) in the RH2180-5 Peak 1 Substance to the RH2180-5 Peak 9 Substance shown in the following Table 1 is a hydroxyl group.

Specifically, R$^1$ in the above formula (1) is preferably a 3-hydroxy-5-methyl-hexanoyl group, a 3-hydroxy-6-methyl-heptanoyl group, or a 3-hydroxy-7-methyl-octanoyl group.

In "the cyclic peptide compound or the pharmaceutically allowable salt thereof" shown by the above formula (1), it is preferable that R$^1$ be a 3-hydroxy-5-methyl-hexanoyl group, R$^2$ a methyl group, and R$^3$ an ethyl group, and that R$^1$ be a 3-hydroxy-7-methyl-octanoyl group, R$^2$ a methyl group, and R$^3$ an ethyl group.

Relationships between R$^1$, R$^2$, and R$^3$ shown in the formula (1) and respective substances are shown in Table 1. Among them, structures of R$^1$, R$^2$, and R$^3$ in the RH2180-5 Peak 5 Substance and the RH2180-5 Peak 9 substance have been established, but structures of R$^1$ in the substances obtained from other peaks have not been completely established; and thus, structural formulae of R$^1$ in Table 1 are mainly from analysis results with an accurate mass spectrometry and from their biosynthesis routes. From the study result of the antibacterial spectra of respective peak substances as mentioned later, tendency that difference in R$^1$ does not pose a significant effect to its antibacterial spectrum is clearly confirmed. Accordingly, these side chains may be at least an acyl group optionally containing a substituent group, or preferably an acyl group having 7 to 9 carbon atoms and optionally containing a substituent group.

<Method for Isolation and Purification of Cyclic Peptide Compounds of the Present Invention>

Method for isolation and purification of cyclic peptide compounds of the present invention is selected with referring to the therapeutic effect in the silkworm *Staphylococcus aureus* infection model; but is not limited to this method. Any method generally used as a method for purification of an intended compound from a culture of a microorganism may be used by appropriately combining them.

Specific example of the method includes extraction by solvent, dissolution to other solvent phase, water precipitation, chromatography by an ODS column and so on, and fractionation by using RP-HPLC with an ODS column and so on. Solvents for extraction and for dissolution to other solvent phase are not particularly restricted; but preferable example thereof includes a water-soluble solvent such as acetone; a hydrophilic solvent such as butanol; a mixed solvent of them; a mixed solvent of water and a hydrophilic solvent; and a mixed solvent of water and a water-soluble solvent. A column packed with a carrier modified with an octyl group or a butyl group, or with a polymer carrier of a polystyrene type, or the like, in place of the ODS column, may be used.

Meanwhile, methods for isolation and purification as mentioned above are mere examples; and thus, any method for isolation and purification may be used provided that an intended novel peptide compound of the present invention can be obtained with the said methods.

<Structural Analysis of Isolated and Purified Cyclic Peptide Compounds of the Present Invention>

When the methods for purification mentioned above are used, 9 compounds can be finally obtained by fractionation with RP-HPLC to give at least 9 peaks from a culture of RH2180-5 (FIG. 1). These belong to a group of compounds in a single fraction in a preliminary stage of the isolation and purification by RP-HPLC. In addition, because of resemblance in UV absorption pattern, they belong to a group of similar compounds.

TABLE 1

| Peak No. | High resolution mass spectrometry | R$^1$ | R$^2$ | R$^3$ |
|---|---|---|---|---|
| P1 | 1603.8612 | CH$_3$(CH$_3$)CHCH$_2$CHOHCH$_2$CO 3-Hydroxy-5-methylhexanoyl | H | CH$_3$CH$_2$ |
| P2 | 1603.8598 | CH$_3$(CH$_3$)CHCH$_2$CHOHCH$_2$CO 3-Hydroxy-5-methylhexanoyl | CH$_3$ | CH$_3$ |
| P3 | 1631.8909 | CH$_3$(CH$_3$)CH(CH$_2$)$_3$CHOHCH$_2$CO 3-Hydroxy-7-methyloctanoyl | H | CH$_3$CH$_2$ |
| P4 | 1631.8917 | CH$_3$(CH$_3$)CH(CH$_2$)$_3$CHOHCH$_2$CO 3-Hydroxy-7-methyloctanoyl | H | CH$_3$CH$_2$ |
| P5 | 1617.8755 | CH$_3$(CH$_3$)CHCH$_2$CHOHCH$_2$CO 3-Hydroxy-5-methylhexanoyl | CH$_3$ | CH$_3$CH$_2$ |
| P6 | 1631.8893 | CH$_3$(CH$_3$)CH(CH$_2$)$_2$CHOHCH$_2$CO 3-Hydroxy-6-methylheptanoyl | CH$_3$ | CH$_3$CH$_2$ |
| P7 | 1631.8920 | CH$_3$(CH$_3$)CH(CH$_2$)$_2$CHOHCH$_2$CO 3-Hydroxy-6-methylheptanoyl | CH$_3$ | CH$_3$CH$_2$ |
| P8 | 1645.9068 | CH$_3$(CH$_3$)CH(CH$_2$)$_3$CHOHCH$_2$CO 3-Hydroxy-7-methyloctanoyl | CH$_3$ | CH$_3$CH$_2$ |
| P9 | 1645.9074 | CH$_3$(CH$_3$)CH(CH$_2$)$_3$CHOHCH$_2$CO 3-Hydroxy-7-methyloctanoyl | CH$_3$ | CH$_3$CH$_2$ |

In Table 1, "High resolution mass spectrometry" is shown by HR TOF MS m/z(M + H)$^+$.

<Method for Preparation of Cyclic Peptide Compounds of the Present Invention>

Method for preparation of cyclic peptide compounds or pharmaceutically allowable salts thereof of the present invention is not particularly restricted; these compounds and the salts thereof may be those produced from a microorganism or chemically synthesized or produced by combination of them.

Figure 3:
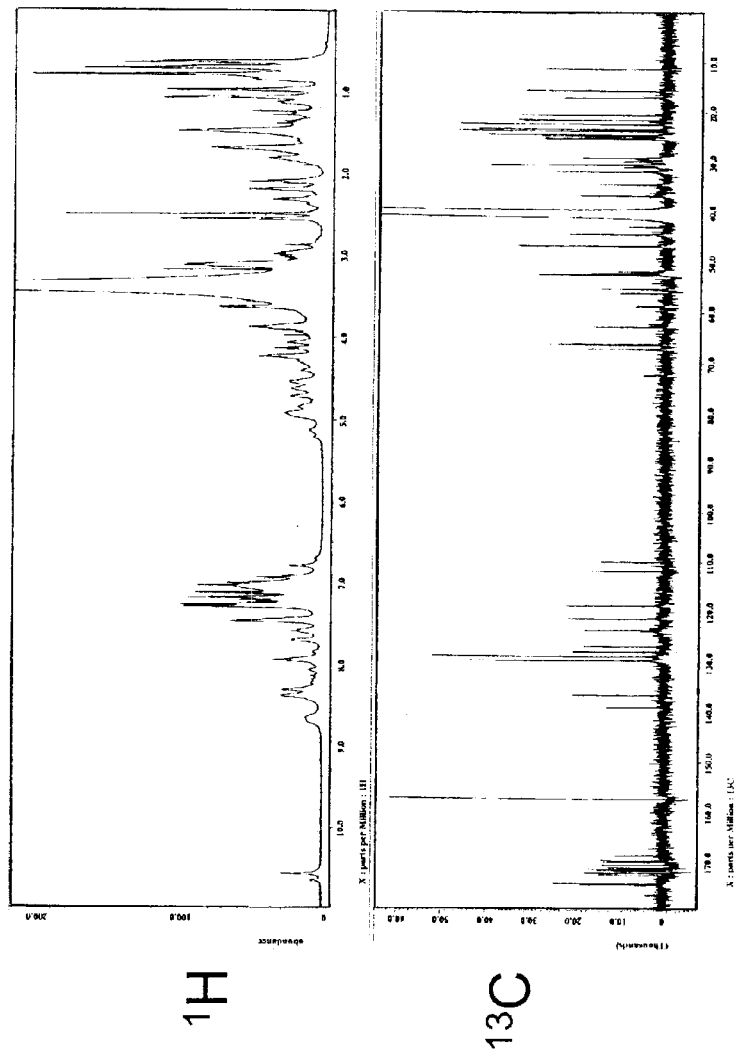
[FIG. 3]
Figure 4:
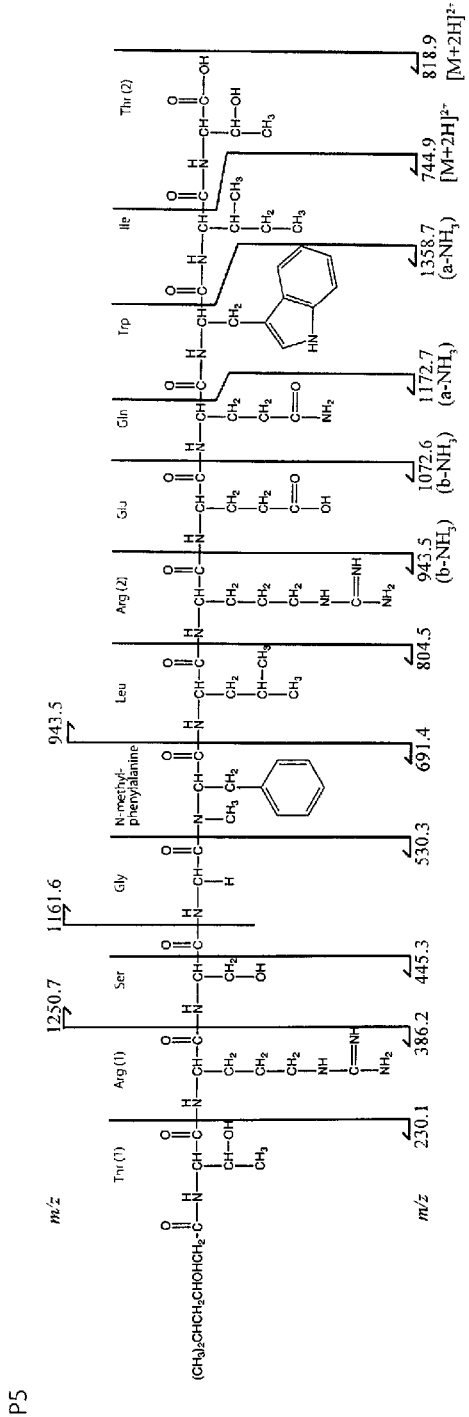
[FIG. 4]
Figure 5:
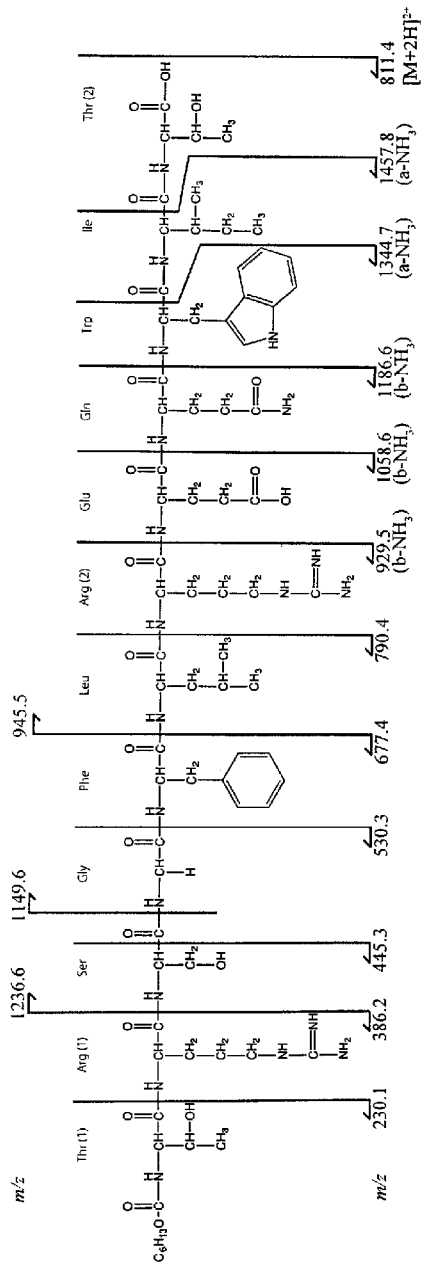
[FIG. 5]
Figure 5:
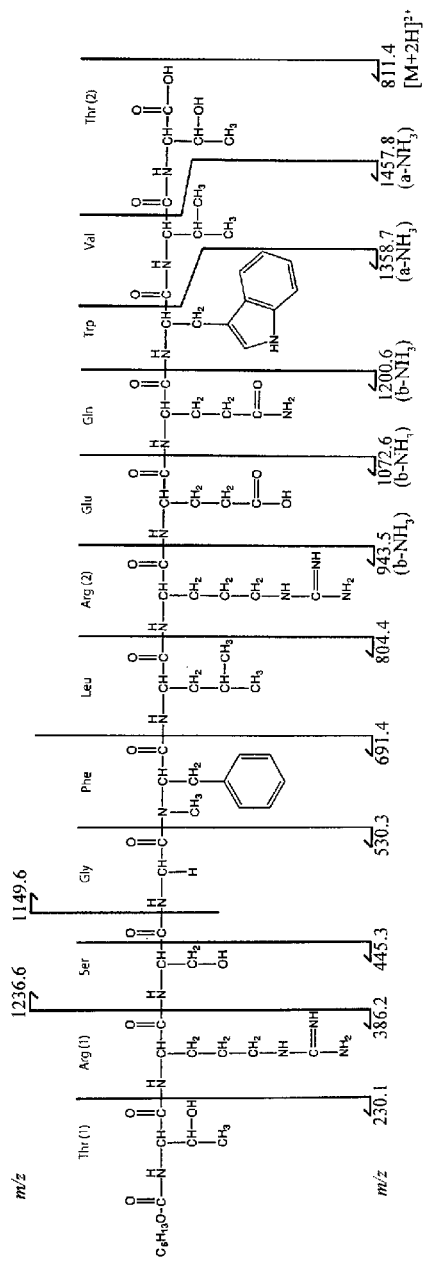
Figure 6:
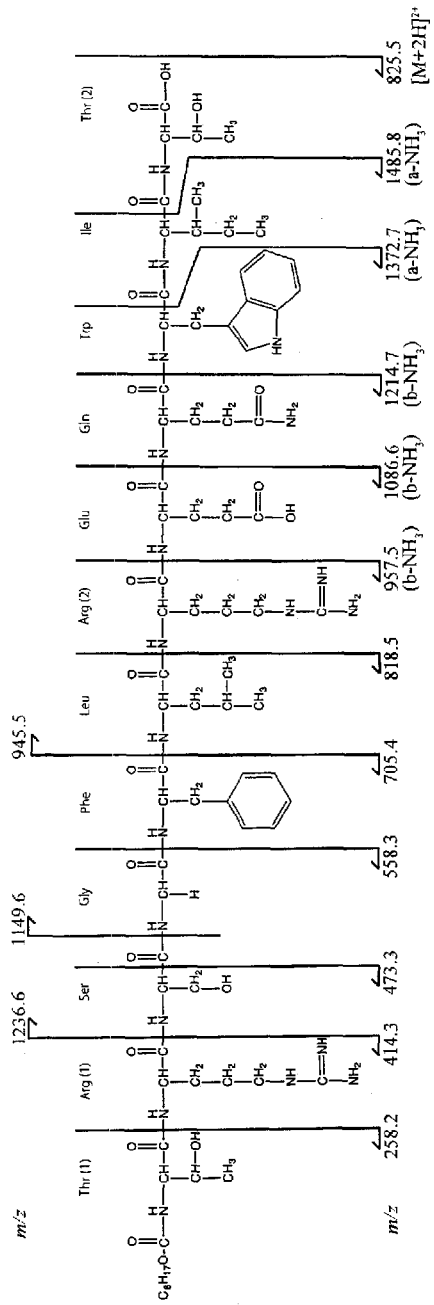
[FIG. 6]
Figure 6:
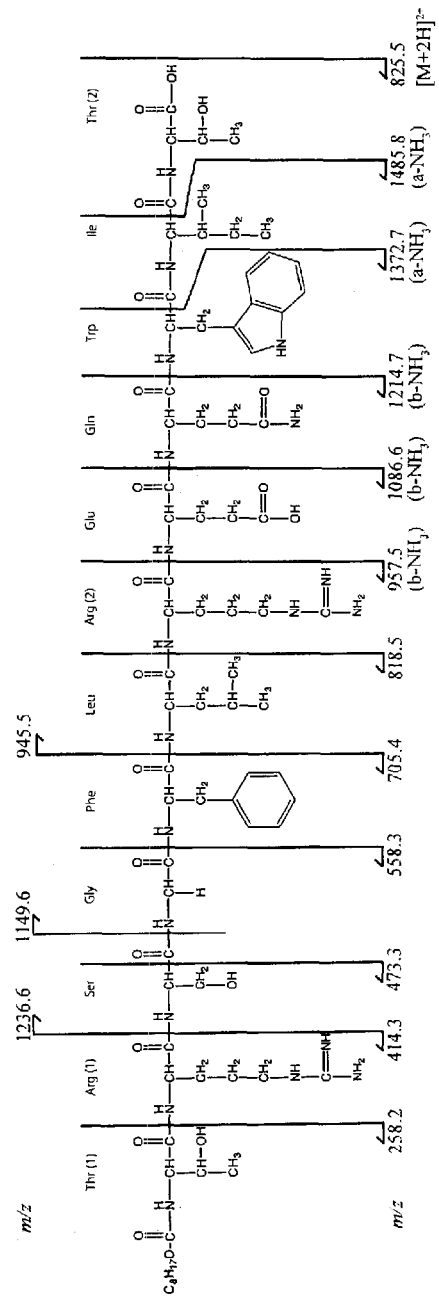
Figure 7:
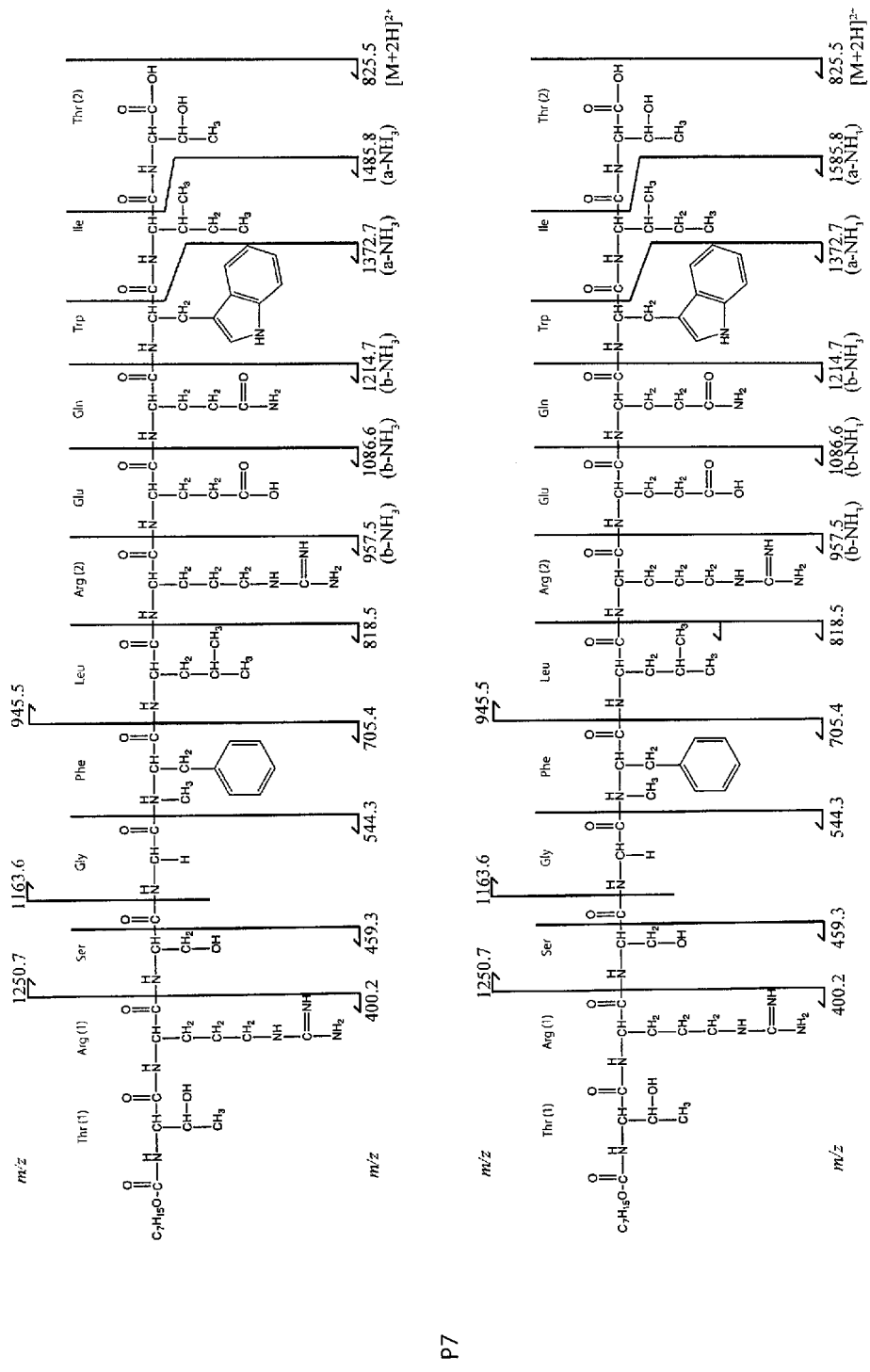
[FIG. 7]

Among these peaks, structural analysis of a purified sample obtained by RP-HPLC from Peak 5, which is a main peak therein, will be explained. Structural analysis thereof may be done by appropriately combining existing structural analysis methods; but the following analysis methods may be efficient. Namely, analysis thereof can be done by an accurate mass spectrometry for molecular weight measurement, amino acid analysis after an acidic hydrolysis treatment (FIG. 2), analysis by $^1$H-NMR and $^{13}$C-NMR (FIG. 3), and TOF-MS analysis (TOF: Time of Flight) (TOF-MS analysis results of Peak 5 are shown in FIG. 4, Peaks 1 and 2 in FIG. 5, Peaks 3 and 4 in FIG. 6, Peaks 6 and 7 in FIG. 7, and Peaks 8 and 9 in FIG. 8). In addition, analysis can be done with a UV spectrum (FIG. 1) and an infrared absorption spectrum (IR).

Figure 2:
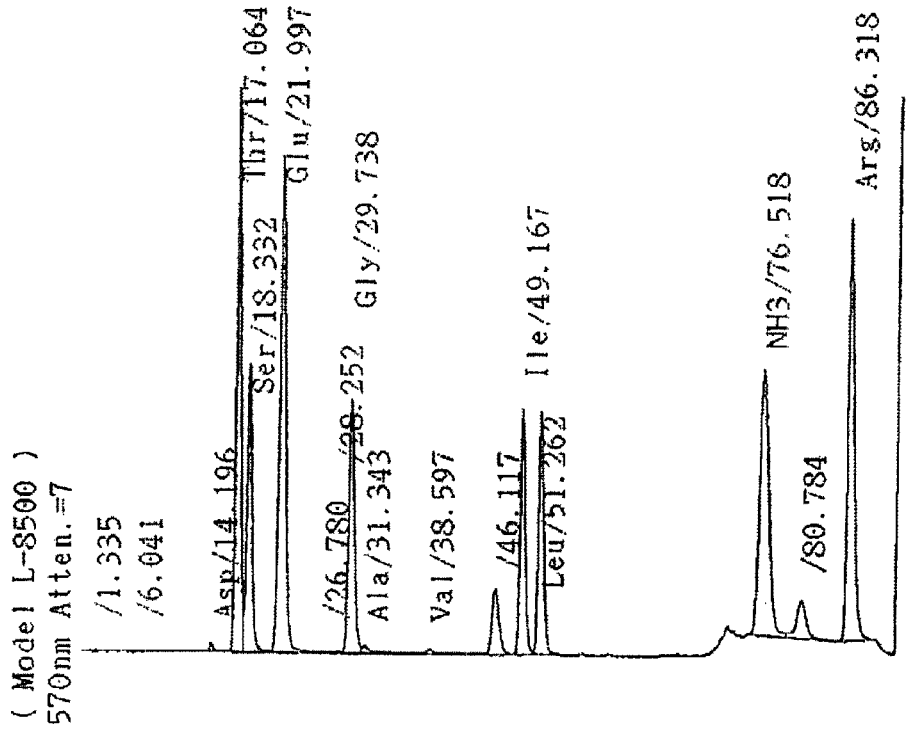
[FIG. 2]

As a result of analysis with the structural analysis methods mentioned above, it was found that the substance obtained from Peak 5 had molecular weight of 1616.9 by the accurate mass spectrometry [(M+H)$^+$ of m/z=1617.8755 by ESI-TOF-MS]; and two molecules as to each of Thr, Glu, Glu, and Arg and one molecule as to each Ser, Gly, and Ile were detected by amino acid analysis (FIG. 2). Then, it was found that the substance finally obtained from the Peak 5 is a novel compound having a novel cyclic peptide skeleton shown by the formula (1) wherein $R^1$ is a 3-hydroxy-5-methyl-hexanoyl group, $R^2$ is a methyl group, and $R^3$ is an ethyl group. This novel compound was given the name of "RH2180-5 Peak 5 Substance" (hereinafter, sometimes shown by "P5" for short).

Similarly to the foregoing, it was confirmed that the substance obtained from the Peak 9 is a compound having number of the carbon atoms of $R^1$ in the RH2180-5 Peak 5 Substance prolonged by two; and then, the substance was given the name of "RH2180-5 Peak 9 substance" (hereinafter, sometimes shown by "P9" for short). In addition, it was found that the substances obtained from other peaks are the compounds having the same cyclic peptide structure as a main skeleton; similarly to the foregoing, they were given the names of "RH2180-5" attached with the Peak number n (hereinafter, sometimes shown by "Pn" for short).

<Physical and Chemical Properties of the Cyclic Peptide Compound RH2180-5 Peak Substance 5 of the Present Invention>

Among the novel compounds having a novel cyclic peptide structure of the present invention as mentioned above, physical and chemical properties of the RH2180-5 Peak 5 Substance are as following.

(1) High resolution mass spectrometry HR TOF MS m/z (M+H)$^+$: 1617.8755
TOF MS analysis (TOF: Time of Flight): FIG. 4
(2) $^1$H-NMR and $^{13}$C-NMR: FIG. 3
(3) Solubility to solvents:
Soluble in water, ethanol, methanol, and acetonitrile
Insoluble in chloroform
(4) Appearance: white powder <Method for Manufacturing Cyclic Peptide Compounds of the Present Invention by Using a Microorganism>

The novel cyclic peptide compounds or pharmaceutically allowable salts thereof of the present invention may be either those obtained by chemical synthesis or those obtained by culturing of a microorganism capable of producing them; and thus, the manufacturing method thereof is not particularly restricted. However, it is preferable that they be manufactured from a culture that is produced by culturing of the RH2180-5 strain, which belongs to a genus *Lysobacter* with Accession No. NITE BP-870 in NITE Patent Microorganisms Depositary (NPMD) of Incorporated Administrative Agency National Institute of Technology and Evaluation (NITE), or by culturing of its mutant strain capable of producing a similar compound to the compound produced from the foregoing strain.

In other words, the present invention is also the cyclic peptide compound shown by the above formula (1) or pharmaceutically allowable salt thereof manufactured from a culture that is produced by culturing of the RH2180-5 strain, which belongs to a genus *Lysobacter* with Accession No. NITE BP-870 in NITE Patent Microorganisms Depositary (NPMD) of Incorporated Administrative Agency National Institute of Technology and Evaluation (NITE), or by culturing of its mutant strain capable of producing a compound similar to the compound produced from the foregoing strain.

<Antibiotic-substance-containing Fraction of the Present Invention>

Further, the present invention is an antibiotic-substance-containing fraction characterized by that the antibiotic-substance-containing fraction is obtained by fractionating a culture which is produced by culturing of a microorganism belonging to a genus *Lysobacter* with Accession No. NITE BP-870 having the base sequence of the 16S rRNA region shown by the Sequence No. 1 in the sequence chart and contains the cyclic peptide compound or the pharmaceutically allowable salt thereof.

Meanwhile, as general characteristic of a bacterium, properties of the strain thereof tend to be mutated easily; and thus, there is a possibility that the properties of RH2180-5 do not stay as they are shown above. However, even a microorganism mutated from RH2180-5 (Accession No. NITE BP-870) is included in RH2180-5 (Accession No. NITE BP-870) as far as the microorganism thus mutated is a microorganism belonging to a genus *Lysobacter* and is capable of producing the antibiotic-substance-containing fraction.

Needless to say, mutation mentioned above includes both natural mutation and artificial mutation.

The antibiotic-substance-containing fraction of the present invention means a fraction obtained by applying some sort of fractionation to a culture which is produced by culturing of the foregoing RH2180-5. Here, the term "culture" means any of culture supernatant, microbial body, crushed body of a cultured microorganism, and so on. "Fractionation" procedure includes every treatment usually applied to a culture with the aim to separate and purify an intended substance, such as extraction, precipitation, separation by membrane, dissolution to other solvent phase, and chromatogram.

As to the use of the antibiotic-substance-containing fraction of the present invention, if an antibiotic substance contained therein shows an antibacterial activity and a therapeutic effect as well, this fraction can be used for manufacturing of a therapeutic drug for an infective disease; and if an antibiotic substance contained therein shows an antibacterial activity but does not show a therapeutic effect, this fraction can be used for manufacturing of a microbial protection agent. The antibiotic-substance-containing fraction which contains an antibiotic substance showing an antibacterial activity but not substantially showing a therapeutic effect is one embodiment of the present invention.

Use method thereof as a microbial protection agent is not particularly restricted; and for example, a method wherein the said fraction is coated, impregnated, or moistened onto surface of a material, a tool, or the like which are required to be antibacterial may be mentioned. More specifically, it may be suitably used, for example, by attaching to or moistening a medical gauze, bandage, and the like, or as an antibacterial ingredient in an adhesive used in various skin adhesive sheet such as a sticking plaster or as an antibacterial ingredient in a topical cream. It is preferable that, in the antibiotic-substance-containing fraction of the present invention, an antibiotic substance contained therein which shows an antibacterial activity but does not substantially show a therapeutic effect be used as a microbial protection agent (the antibiotic substance is preferably any one of being used as a microbial protection agent and having properties to be used as a microbial protection agent or both).

Usually, an antibiotic substance is difficult to be used as a microbial protection agent because it is necessary to pay attention to emergence of a multiple-drug-resistant bacterium; but, the antibiotic-substance-containing fraction of the present invention which does not show a therapeutic effect and the antibiotic substance obtained therefrom can be used as a microbial protection agent without such worries. When used as a microbial protection agent, the antibiotic-substance-containing fraction may be used as it is, or only after concentration of the said fraction; or alternatively, an antibiotic substance after separated and purified may be used. These treatments may be selected in accordance with their respective uses.

As mentioned above, the antibiotic-substance-containing fraction of the present invention can be obtained by fractionation of a culture which is obtained by culturing of RH2180-5, regardless whether a therapeutic effect exists or not.

The microorganism which produces the antibiotic-substance-containing fraction and an antibiotic substance obtained from each fraction thereof in the present invention is selected from many microorganisms separated from soils of Okinawa by evaluating an antibacterial activity with MIC and a therapeutic effect with a method that uses the silkworm *Staphylococcus aureus* infection model described in Patent Document 4.

<With Regard to the Microorganism RH2180-5 of the Present Invention>

Hereinafter, the microorganism RH2180-5 of the present invention will be explained in detail. The microorganism which belongs to a genus *Lysobacter* and is given the name of "RH2180-5 strain" (hereinafter, shown as "RH2180-5") was newly discovered. This RH2180-5 was deposited domestically on Jan. 25, 2010 to the NITE Patent Microorganisms Depositary (NPMD) of Incorporated Administrative Agency National Institute of Technology and Evaluation (hereinafter, abbreviated as "NITE"), the address of which is 2-5-8 Kazusakamatari, Kisarazu-shi, Chiba, with the Accession No. "NITE P-870".

"RH2180-5" was then transferred to the international deposition (transfer date (international deposition date): May 20, 2011) from the domestic deposition (original deposition date: Jan. 25, 2010) by presenting the original deposition request form to the NITE Patent Microorganisms Depositary (NPMD) of Incorporated Administrative Agency National Institute of Technology and Evaluation (NITE), the address of which is 2-5-8 Kazusakamatari, Kisarazu-shi, Chiba, with the transfer request furnished with life guarantee to the international deposition in accordance with Budapest Treaty; as a result of acceptance of the transfer request, it was give Accession No. "NITE BP-870".

The microorganism of the present invention belongs to a genus *Lysobacter* with Accession No. NITE BP-870 or is a naturally or artificially mutated microorganism thereof, and is capable of producing an antibiotic substance having an antibacterial activity. This was identified as a novel microorganism belonging to a genus *Lysobacter* from properties and sequence of the 16S rRNA region of this strain as mentioned later.

Morphology:

This RH2180-5 is a gram-negative *bacillus* not having a flagellum while showing a gliding property. Fructification is not found. Acidophile is not shown.

Growth Situation in Culture Medium:
(1) A pale yellow colony is formed on a broth agar flat plate. Diffusing color pigments are not found.
(2) In stab culture with a broth gelatin medium, the microorganism grows thereinto with liquidizing a gelatin.

Physiological Properties:

Physiological and chemical classification properties of RH2180-5 are as following.
(1) Growth pH (optimum growth pH): 5 to 9 (6 to 8)
(2) Growth temperature (optimum growth temperature): 10 to 40° C. (25 to 30° C.)
(3) Behavior to oxygen; aerobiotic
(4) MR test (Methyl red test): –
(5) VP test (Voges-Proscauer test): +
(6) Pigment formation: +
(7) Oxidase test: +
(8) Catalase test: +
(9) Urease test: –
(10) Phosphatase test: +
(11) Casein hydrolysis: +
(12) Cellulose hydrolysis: –
(13) Gelatin hydrolysis: +
(14) Starch hydrolysis: –
(15) Deoxyribonuclease test: +
(16) Nitrate reduction: –
(17) Denitrification: –
(18) H$_2$S production: —
(19) Indole production: –
(20) Citrate utilization: +
(21) OF-test: oxidation
(22) Production ability of an acid and a gas from the following sugars and so on:
   L-Arabinose: –
   D-Xylose: –
   D-Glucose: +
   D-Mannose: +
   D-Fructose: +
   D-Galactose: –
   D-maltose: +
   D-Sucrose: +
   D-Lactose: +
   D-Trehalose: +
   D-Sorbitol: –
   Glycerol: –
   Starch: –

Molecular Biological Analysis Results:

Analysis results of RH2180-5 with regard to 16S rRNA in accordance with guidance of the molecular biological systematic classification are as following.

<<16S rRNA Sequence>>

(12) Analysis Results of the 16S rRNA Sequence

Base sequence of the 16S rRNA region from the RH2180-5 colony was amplified by a colony PCR and then it was analyzed by a sequencer; and as a result, base sequence of almost entire length of the 16S rRNA except for some bases at the 5' terminal side and the 3' terminal side could be obtained. This base sequence is shown in the Sequence No. 1 in the sequence chart. Because the base sequence in the Sequence No. 1 in the sequence chart is not obtained from the entire length of 16S rRNA, the term 16S rRNA "region" is used. When homology search of this base sequence was executed by NCBI BLAST, the base sequence of the 16S rRNA region of RH2180-5 showed homology rate of 99% relative to the base sequence of *Lysobacter enzymogenes* DSN2043T strain, which belongs to a genus *Lysobacter*. Meanwhile, there is no report that this *Lysobacter enzymogenes* produces an antibiotic substance; and thus, this is different from RH2180-5.

By referring the properties of RH2180-5 as mentioned above to classification according to Bergey's Manual of Systematic Bacteriology, Vol. 3, 1989 and to descriptions in other references, together with analysis results of 16S rRNA, RH2180-5 was comprehensively judged to be a microorganism belonging to a genus *Lysobacter*.

<Novelty and so on of RH2180-5>

RH2180-5 was judged to be a novel microorganism strain in comprehensive consideration of the facts including the following: a microorganism which has the base sequence of the 16S rRNA region identical to the base sequence of the 16S rRNA region of RH2180-5 does not exist; compounds produced from RH2180-5 are novel compounds having a basic skeleton of a novel cyclic peptide structure as mentioned above; these compounds show an antibacterial activity not only to MRSA but also to VRE, and a therapeutic effect thereof to an infective disease by MRSA could be confirmed in a mouse; some of antibiotic substances produced from RH2180-5 (this will be mentioned later) have an antibacterial spectrum showing an antibacterial activity not only to MRSA but also to VRE (this has been scarcely reported before); higher therapeutic effect to an infective disease by *Staphylococcus aureus* as compared with vancomycin is shown; and a novel antibiotic substance having high usefulness not reported before is produced.

RH2180-5 was deposited internationally to the NITE Patent Microorganisms Depositary (NPMD) of Incorporated Administrative Agency National Institute of Technology and Evaluation (NITE) with Accession No. NITE BP-870 (original deposition date of Jan. 25, 2010, and international deposition date (transfer date) of May 20, 2011), so that it can be obtained therefrom. Meanwhile, as the general characteristics of a bacterium, properties of the strain thereof tend to be mutated easily; and thus, there is a possibility that the physiological properties of RH2180-5 do not stay as they are shown above. Further, needless to say, "mutation" mentioned above includes both natural mutation and artificial mutation. Even a mutant microorganism from RH2180-5 (Accession No. NITE BP-870) is included in the microorganism of the present invention as far as it is capable of producing the antibiotic substance. The cyclic peptide compound shown by the above formula (1) of the present invention includes those produced from the mutant microorganism from RH2180-5 (Accession No. NITE BP-870). The antibiotic-substance-containing fraction and the antibiotic substance obtained therefrom of the present invention can be obtained from a culture of this RH2180-5.

Namely, the microorganism of the present invention is a microorganism which belongs to a genus *Lysobacter* with Accession No. NITE BP-870 or is a naturally or artificially mutated microorganism thereof, and in addition, is capable of producing an antibiotic substance showing an antibacterial activity. Further, the microorganism of the present invention is a microorganism which has the base sequence of the 16S rRNA region shown by the Sequence No. 1 in the sequence chart. Preferably, the microorganism of the present invention is a microorganism which is capable of producing the compound shown by the above formula (1) or the salt thereof.

More preferably, the microorganism of the present invention is the foregoing microorganism, wherein the antibiotic substance produced therefrom has an antibacterial activity to at least methicillin-resistant *Staphylococcus aureus* (MRSA) and vancomycin-resistant *Enterococcus* (VRE). In other words, the NITE BP-870 microorganism capable of producing an antibiotic substance having an antibacterial activity to at least MRSA and VRE and the mutant microorganism from NITE BP-870 are included in the more preferable microorganism of the present invention. In addition, needless to say, the mutation thereof includes natural mutation and artificial mutation.

<Method for Culturing of RH2180-5>

Hereinafter, a method for culturing of RH2180-5 will be described. Culturing of RH2180-5, which produces a novel compound having a novel cyclic peptide structure, the antibiotic-substance-containing fraction, and so on of the present invention, may be done in accordance with a general method for culturing of an microorganism belonging to a genus *Lysobacter*. Specifically, RH2180-5 is inoculated to a nutrient source culture medium such as a YME culture medium, a SGM culture medium, a CDY culture medium, and a YPGM culture medium, and then, it is cultured under an aerobatic condition. As to the carbon source in the culture medium, organic carbon compounds such as D-glucose, D-fructose, sucrose, starch, dextrin, glycerin, molasses, glutinous starch syrup, and fat oil are used. As to the nitrogen source, organic and inorganic nitrogen compounds such as meat extract, casein, peptone, yeast extract, dry yeast, germ, powdered soybean, urea, an amino acid, and an ammonium salt may be used. In addition, inorganic salts such as a sodium salt, a potassium salt, a calcium salt, a magnesium salt, a phosphate salt, an iron salt, a copper salt, a zinc salt, and cobalt salt may be added as necessary. Further, addition of a growth accelerator such as biotin, vitamin B1, cystine, methyl oleate, and lard oil is preferable in order to increase production amount of the intended substance. In addition, an antifoaming agent such as a silicone oil and surfactant may be added.

As to the culture condition, it is preferable that culture be done under an aerobic condition as mentioned before. In the case of liquid culturing, culturing with an aerated agitation method is preferable. In the case of culturing in a small scale, culturing with shaking by a flask may be used. It is possible that culturing be done at 20 to 40° C.; but it is preferable to keep the temperature at 25 to 35° C., or more preferably near 30° C. As to the pH during culturing, pH 6 to 8 is preferable, though pH of around 7 is particularly preferable. Culturing time is variable depending on the factor such as culture medium used and culture temperature; but in the case of RH2180-5, culturing time is usually in the range of about 1 to about 20 days, or preferably in a short time of about 3 to 7 days, during which time sufficient amount of the intended substance can be secured.

<Purification Method of Antibacterially Active Component>

Recovery of an antibacterially active component from a culture of RH2180-5 may be done with a usual method for recovery and purification of a physiologically active substance from culture of a microorganism. Here, the culture includes culture supernatant, microbial body, crushed body of a cultured microorganism, and so on. For example, after suspension is formed by adding an appropriate organic solvent such as acetone to a culture for extraction treatment, a microbial body is removed by centrifugal separation, membrane separation, or the like to obtain an extraction supernatant, which may be then subjected to the isolation and purification treatments. As necessary, residual microbial body may be further subjected to re-extraction after such treatment as frictional crushing.

Usually, extraction solvent used in separation and purification of an intended substance and method for separation and purification thereof are selected with referring to concentration degree of the antibacterial activity judged by MIC. In mere separation and concentration of an antibacterial active component, there is no problem with it basically. However, in separation and purification of an antibiotic-substance-containing fraction and an antibiotic substance which are produced from RH2180-5 of the present invention, selection of the foregoing matters are done with referring not only to the MIC result but also to the therapeutic effect with the silkworm *Staphylococcus aureus* infection model shown in Patent Document 4. As a result, concentration and purification of "the novel antibiotic substance produced from RH2180-5" could be achieved, despite that these operations have been considered difficult when referring only to the MIC result. Accordingly, this matter will be described next.

<Separation and Purification of Antibiotic Substances with Referring to the Therapeutic Effect Based on the Silkworm *Staphylococcus Aureus* Infection Model>

(Narrow Down of Effective Strains by MIC)

In the present invention too, a first screening to narrow down effective strains from several tens of thousands of extraordinary large numbers of strains may be done by any method as far as the antibacterial activity can be evaluated with the said method; and thus, for example, by referring to MIC, test bodies showing the antibacterial activity to *Staphylococcus aureus* in culture supernatant of each strain may be picked up. This is because strains not showing the antibacterial activity at all are not in the scope of examination. Any method capable of evaluating the antibacterial activity may be used; but a method with which a strain recognized to show, with referring to MIC, the antibacterial activity to *Staphylococcus aureus* in culture supernatant of various test strains is picked up is preferable. Thereafter, when number of the strains is narrowed down to several thousands to several hundreds, evaluation of the therapeutic effect of the antibiotic-substance-containing fraction and the antibiotic substance obtained therefrom may be studied by measuring $ED_{50}$ thereof by using the silkworm *Staphylococcus aureus* infection model.

Strains recognized to show the therapeutic effect in the silkworm *Staphylococcus aureus* infection model are further subjected to various separation and purification treatments wherein the therapeutic effect is evaluated in each operation by using the silkworm *Staphylococcus aureus* infection model. Further, concentration degree of the therapeutic effect depending on kind and method of separation and purification operations by administering the antibiotic-substance-containing fraction of each purification stage is confirmed by using the silkworm. *Staphylococcus aureus* infection model. By doing so, kind and method of separation and purification operations with which "therapeutic effect" can be effectively concentrated are selected.

"Selection of strain and method for separation and purification operations with referring to the therapeutic effect" as mentioned above by using an experimental animal such as mouse is practically impossible in view of problems of procedure, cost, and ethics; and thus, these could be achieved for the first time by utilizing the silkworm *Staphylococcus aureus* infection model (see, Example 1).

Results in Table 2 summarize the antibacterial activity MIC and the therapeutic effect $ED_{50}$ by the silkworm infection model of test bodies in each purification stage from culture of RH2180-5 to be purified. In Table 2, total activity "unit" is defined as the activity necessary for 50% of the survival probability of one-gram body weight of silkworms infected to *Staphylococcus aureus*.

As shown in Table 2, very interestingly, it became clear that, depending on isolation and purification operations, concentration degree of the antibacterial activity does not necessarily coincide with concentration degree of the therapeutic effect. Results of Table 2 show that $ED_{50}$ was concentrated by 300-folds, while MIC was concentrated only by 5-folds according to the isolation and purification methods employed herein.

25 to 5 with this separation and purification method. It is also shown that recovery yield of the therapeutic effect reaches nearly 30% in two peaks relative to 100% in the acetone extract in spite of the fact that recovery yield thereof based on % by mass is only 0.1%.

Further, it is presumed that the residual matters after the acetone extraction contains relatively large amount of antibiotic substances showing the antibacterial activity but not showing the therapeutic effect; and thus, they may be used as the antibiotic-substance-containing fraction showing the antibacterial activity but not substantially showing the therapeutic effect by recovering and concentrating them.

RH2180-5 was discovered effectively by using the separation and purification method by referring to the therapeutic effect based on the silkworm *Staphylococcus aureus* infection model. This is because, if separation and purification of an intended substance is done by referring only to the antibacterial activity, which has been done previously, the antibacterially active component not showing the therapeutic effect is concentrated, so that it may be presumed from the results of Table 2 that there is high possibility of missing an antibiotic substance which has high therapeutic effect in a living body. In this case, usefulness of RH2180-5 cannot be confirmed, so that it is highly probable that RH2180-5 itself has been missed. Accordingly, to provide the novel microorganism (RH2180-5), it is a very important point in the present invention that selection was done by referring to the therapeutic effect based on the silkworm. *Staphylococcus aureus* infection model.

(Evaluation of Antibacterial Activity by the Minimum Inhibitory Concentration MIC)

Antibacterial activity of the antibiotic-substance-containing fraction at each fractionation stage from a culture produced from RH2180-5 and that of the antibiotic substance obtained therefrom by separation and purification thereof can be evaluated by MIC. Measurement of MIC is done by a generally recognized standard method. For example, it is done with a broth microdilution method based on CLSI (formerly NCCLS: National Committee for Clinical Laboratory Standards).

Judgment standard for sensitivity is different depending on strains; and thus, in accordance with judgment standards stipulated by CLSI, classification is made to respective categories, namely S for sensitive, I for intermediate, and R for resistant.

TABLE 2

Purification by referring to the therapeutic effect by using the silkworm *Staphylococcus aureus* infection model

|  | Total activity (unit) | Recovery yield (%) | Weight (mg) | Weight (%) | $ED_{50}$ (μg/g-larva) | MIC (μg/mL) |
|---|---|---|---|---|---|---|
| Aceton extract | 87000 | 100 | 8100 | (100) | 90 | 25 |
| Butanol extract | 88000 | 100 | 340 | (4) | 4 | 0.6 |
| Water precipitation | 41000 | 47 | 80 | (1) | 1.8 | N.D. |
| ODS column chromagtoraphy RP-HPLC | 45000 | 51 | 22 | (0.2) | 0.5 | N.D. |
| peak5 | 16000 | 18 | 5.3 | (0.06) | 0.3 | 5 |
| peak9 | 10000 | 11 | 3.5 | (0.04) | 0.3 | 5 |

Purification from 1200 mL culture.
N.D.: not determined

Results of Table 2 show that $ED_{50}$ is concentrated by 300-folds from 90 in the acetone extraction stage to 0.3 in the fractionated peaks of the final purification stage by RP-HPLC, while MIC is concentrated by only 5-folds from (With Regard to the Antibiotic-substance-containing Fraction)

Here, the term "antibiotic-substance-containing fraction" of the present invention obtained by fractionation of a culture which is produced by culturing of RH2180-5 (Accession No. NITE BP-870) means any of the following fractions; a fraction containing an antibiotic substance showing any one of the antibacterial activity and the therapeutic effect or both and obtained by fractionation of a culture of RH2180-5; a fraction obtained by separating and purifying a part of substances contained in the foregoing fraction; a fraction obtained by partially purifying an antibiotic substance contained in the separated and purified fraction; and a fraction containing an antibiotic substance purified to its pure state.

Further, the acetone extract and the butanol extract in Table 2, especially the butanol extract is considered to be the antibiotic-substance-containing fraction which contains a large amount of the antibiotic substance showing the antibacterial activity but not showing or sparsely showing the therapeutic effect as compared with the antibiotic substance contained in the 9 peaks (antibiotic-substance-containing fractions) described in the later-mentioned Table 4 in view of low concentration degree of the antibacterial activity in the subsequent purification processes and high concentration degree of the therapeutic effect on the other hand. The fraction like this is usually considered low in its usefulness; but it is high in its usefulness for the reason described below, and thus, it can be considered that this is included in the antibiotic-substance-containing fraction of the present invention.

That is, when the antibiotic substance having a high antibacterial activity is used as a therapeutic drug for an infective disease, its use must be closely examined as to its necessity in the light of emergence of a multiple-drug-resistant bacterium. On the other hand, when this antibiotic substance is used as an antibacterial agent such as a microbial protection agent, it is difficult to restrict its usage because the use thereof tends to be naturally abusus because of its use embodiments; and thus, a therapeutic antibiotic substance is not used for a microbial protection agent even if it has a high antibacterial activity.

However, the antibiotic-substance-containing fraction of the present invention which contains a large amount of the antibiotic substance showing the antibacterial activity but not showing or sparsely showing the therapeutic effect evaluated by the silkworm. Staphylococcus aureus infection model or other microbial infection model, and the antibiotic substance obtained therefrom as the antibiotic substance showing the antibacterial activity but not showing or sparsely showing the therapeutic effect can be used in vitro use such as a microbial protection agent. This is because these antibiotic-substance-containing fractions are not used as a therapeutic drug for an infection disease; and thus, there is no need to pay attention to emergence of a multiple-drug-resistant bacterium. In the present invention, showing the antibacterial activity but "not substantially showing the therapeutic effect" means not showing the therapeutic effect to the degree that it can be used as a therapeutic drug.

To separate and purify this antibiotic substance not substantially showing the therapeutic effect, the same evaluation methods as those of the foregoing antibiotic substance showing the therapeutic effect may be used; specifically, methods with which an antibiotic substance showing the antibacterial activity by MIC but not showing or sparsely showing the therapeutic effect by an infective disease model can be separated and purified may be selected. Here, the foregoing infective disease model is not particularly restricted; but similarly to the antibiotic substance showing the therapeutic effect, the infection disease model using a silkworm, such as the silkworm Staphylococcus aureus infection model, can be used preferably.

Further, separation and purification of the antibiotic substance not showing the therapeutic effect may be done only for its own sake; but it is preferable to utilize the investigation results on the methods of separation and purification of the antibiotic substance showing the therapeutic effect. That is, a method for recovering the antibiotic substance showing the therapeutic effect is used to the antibiotic-substance-containing fraction and then methods for concentration, separation, and purification of the antibiotic substance not showing the therapeutic effect is used to the residue thereof; by so doing, the antibiotic substance showing the antibacterial activity but not showing the therapeutic effect can be separated and purified without special investigation.

Next, method for separation and purification of an antibiotic substance from the antibiotic-substance-containing fraction will be described by referring to the example of separation and purification of the antibiotic substance showing the therapeutic effect.

(Method for Separation and Purification of an Antibiotic substance)

A method for separation and purification by referring to the therapeutic effect base on the silkworm Staphylococcus aureus infection model is not particularly restricted; methods such as solvent extraction of culture, dissolution to other solvent phase, water precipitation, chromatography by an ODS column and so on, and fractionation by using RP-HPLC with an ODS column and so on may be mentioned. Solvents for solvent extraction and for dissolution to other solvent phase are not particularly restricted; but preferable example thereof includes a water-soluble solvent such as acetone; a hydrophilic solvent such as butanol; a mixed solvent of them; a mixed solvent of water and a hydrophilic solvent; and a mixed solvent of water and a water-soluble solvent. A column packed with a carrier modified with an octyl group or a butyl group, or a column packed with a polymer carrier of a polystyrene type, or the like, in place of the ODS column, may be used (see Table 2).

Meanwhile, methods for isolation and purification as mentioned above are mere examples; and thus, any method for isolation and purification may be used provided that an intended antibiotic-substance-containing fraction and antibiotic substance can be finally obtained with the said method.

(Structural Analysis of Antibiotic Substances Separated and Purified)

By RP-HPLC as mentioned above, compounds fractionated into 9 peaks (these correspond to the antibiotic-substance-containing fractions) could be separately obtained from the culture of RH2180-5 (FIG. 1). Because these have similar UV absorption patterns, they are similar compounds with each other and constitute one component before the RP-HPLC stage depending on method of separation and purification.

As to the analysis method for chemical structures of the antibiotic substances contained in these peaks, there is no particular restriction; and thus, an arbitrary method may be used. For example, structural analysis of the sample of Peak 5, which is a main peak of those 9 peaks purified with RP-HPLC, was done by the following analysis methods.

Namely, as a result of analysis thereof by an accurate mass spectrometry for molecular weight measurement, amino acid analysis after an acidic hydrolysis treatment (FIG. 2), analysis by $^1$H-NMR and $^{13}$C-NMR (FIG. 3), and TOF-MS analysis (TOF: Time of Flight) (FIG. 4), and so on, two molecules as to each of Thr, Glu, Glu, and Arg and one molecule as to each of Ser, Gly, and Ile were detected (FIG. 4); and thus, it was found to be a novel antibiotic substance having a novel skeleton structure shown by FIG. 9 (hereinafter, this is described as "RH2180-5 Peak 5 Substance").

(Antibacterial Spectrum)

Antibacterial spectrum of the antibiotic substance contained in each of the peaks can be studied by MIC as mentioned above. By so doing, for example, the RH2180-5 Peak 5 Substance showed antibacterial activity to gram-positive bacteria such as Staphylococcus aureus and Enterococcus faecalis, as shown in Table 3 of Test Example 1. In addition, this substance showed an antibacterial activity to not only methicillin-resistant *Staphylococcus aureus* (MRSA) but also vancomycin-resistant *Enterococcus* (VRE), and thus, it was confirmed that this is also effective to multiple-drug-resistant bacteria (see, Table 3).

Further, antibiotic substances contained in Peak 6 and Peak 9 also showed the same antibacterial spectrum to MRSA and VRE as that of the RH2180-5 Peak 5 Substance (see, Table 3).

Antibacterial activity of the antibiotic substances contained in Peak 2, Peak 3, Peak 4, Peak 7, and Peak 8, except for Peak 1, to the multiple-drug-resistant bacteria and to the bacterium not showing chemical resistance was investigated; and as a result, similarly to the antibiotic substances contained in Peak 5, Peak 6, and Peak 9, antibiotic substances contained in these peaks showed the same antibacterial activity to the multiple-drug-resistant bacteria and to the bacterium not showing chemical resistance; and thus, it could be confirmed that they are not influenced by the multiple-drug-resistance (see, Table 4 of Test Example 2).

Consequently, it can be confirmed that the antibiotic substance having a therapeutic effect which is contained in the antibiotic-substance-containing fraction of the present invention is an antibiotic substance characterized by that it is obtained from a culture of RH2180-5 (Accession No. NITE BP-870), the antibiotic substance produced from the said microorganism, and has an antibacterial activity to MRSA and VRE.

<Therapeutic Effect in the Mouse *Staphylococcus aureus* infection model>

It is confirmed that the antibiotic substance produced from RH2180-5 has the therapeutic effect in the silkworm *Staphylococcus aureus* infection model in each purification step. In Patent Document 4, it is confirmed that a substance showing the therapeutic effect in the silkworm *Staphylococcus aureus* infection model also shows the therapeutic effect in the mouse infection model. Therefore, similar confirmation was made to the RH2180-5 Peak 5 Substance; and as a result, the RH2180-5 Peak 5 Substance showed the therapeutic effect in the mouse infection model either, and that $ED_{50}$ value thereof was 0.6 mg/kg, which is clearly lower than 1.6 mg/kg of vancomycin, so that it was confirmed that this has a high therapeutic effect (see, Table 5 of Test Example 3).

Result of the acute toxicity test to a mouse showed that mouse was not killed with dose amount of 50 mg/kg; and thus, the RH2180-5 Peak 5 Substance is low in toxicity.

From the results shown above, it could be confirmed that the antibiotic RH2180-5 Peak 5 Substance produced from RH2180-5 of the present invention shows more excellent $ED_{50}$ value to *Staphylococcus aureus* as compared with vancomycin whereby showing high therapeutic effect while having excellent characteristics of showing effectiveness not only to MRSA but also to VRE, which are clinically very problematic germs.

Namely, the antibiotic-substance-containing fraction produced from RH2180-5 of the present invention contains an antibiotic substance showing the therapeutic effect to an infective disease at least due to *Staphylococcus aureus*; and in addition, this antibiotic substance shows the therapeutic effect to the foregoing infective disease in the same level or higher as compared with vancomycin.

Further, substances in other peaks (corresponding to antibiotic substances in the antibiotic-substance-containing fractions) also show the antibacterial spectra (confirmed in Peak 6 and Peak 9) and UV spectra similar to those of the RH2180-5 Peak 5 Substance, suggesting that these are similar compounds to the RH2180-5 Peak 5 Substance. Accordingly, it is presumed that the therapeutic effects thereof tend to be the same as that of the RH2180-5 Peak 5 Substance.

Similarly to the sample purified from the Peak 5 by RP-HPLC, structural analysis of other peaks were done with an accurate mass spectrometry for molecular weight measurement, amino acid analysis after an acidic hydrolysis treatment, analysis by $^1$H-NMR and $^{13}$C-NMR, TOF-MS analysis, a UV spectrum, and an infrared absorption spectrum (IR); and as a result, they were the compounds shown by the following formula (1) and in Table 1.

[Chem. 5]

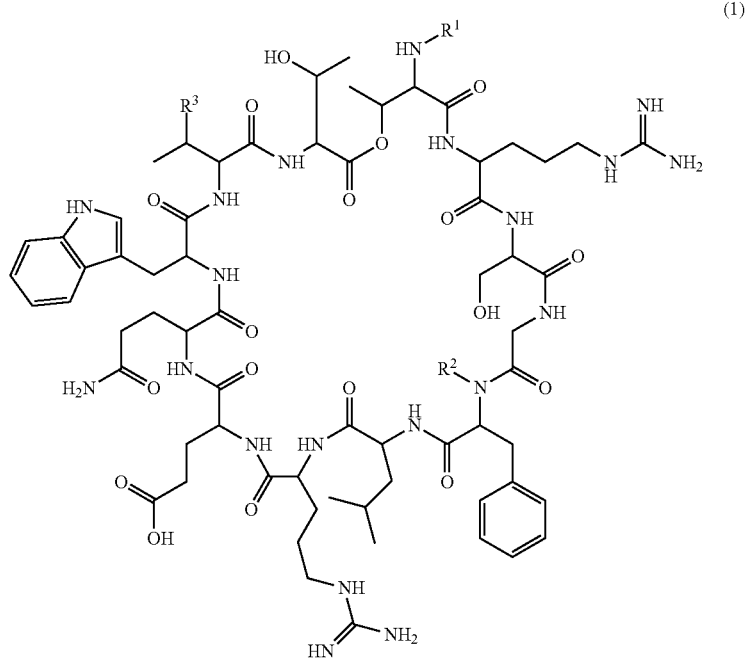

(1)

(In the formula (1), $R^2$ represents an acyl group having 7, 8, or 9 carbon atoms and containing one hydroxyl group; $R^2$ represents a methyl group or a hydrogen atom; and $R^3$ represents an ethyl group or a methyl group.)

The present invention is preferably the foregoing antibiotic substances shown by the above formula (1), and the antibiotic substance shown by the above formula (1) is particularly preferably the substances shown in the above Table 1.

The method to separate and purify any one of the antibiotic substance showing an antibacterial activity and the antibiotic substance showing an therapeutic effect to an infective disease or both from a culture which is produced by culturing of the foregoing RH2180-5 (Accession No. NITE BP-870) and contains the foregoing cyclic peptide compound or the salt thereof can be used as the method for manufacturing an useful antibiotic substance. The said RH2180-5 (Accession No. NITE BP-870) has the base sequence of the 16S rRNA region shown by the Sequence No. 1 in the sequence chart.

In addition, this method can be used as the method for manufacturing an antibiotic substance, wherein the antibiotic substance shows an antibacterial activity to both methicillin-resistant *Staphylococcus aureus* (MRSA) and vancomycin-resistant *Enterococcus* (VRE).

Further in addition, the present invention can be used as the method for manufacturing an antibiotic substance, wherein the antibiotic substance shows an antibacterial activity to MRSA and VRE, and further shows a therapeutic effect to an infective disease at least due to *Staphylococcus aureus*.

The antibiotic-substance-containing fraction obtained by fractionating a culture which is produced by culturing the microorganism with Accession No. NITE BP-870 is useful. In addition, the microbial protection agent which contains the antibiotic substance obtained from this culture is useful. Further, the microbial protection agent which contains the fraction before isolation of a substance as the substance is useful.
<Preparation Method of the Cyclic Peptide Compound of the Present Invention from a Culture of RH2180-5>

As to the method for obtaining "the cyclic peptide compound shown by the foregoing formula (1)" of the present invention from a culture of RH2180-5, a conventional method to obtain a physiologically active substance from a culture of a microorganism may be mentioned. Here, the term "culture" means the same as mentioned before.

To prepare "the cyclic peptide compound shown by the foregoing formula (1)" of the present invention, methods for isolation and purification thereof are selected not only by usually used confirmation of the antibacterial activity by MIC but also by referring to the therapeutic effect ($ED_{50}$) as an indicator by using the silkworm *Staphylococcus aureus* infection model described in Patent Document 4 (see, Table 2).

That is, it can be assumed that the cyclic peptide compound shown by the foregoing formula (1) of the present invention could be effectively discovered by using the isolation and purification methods which were selected by referring to not only MIC but also the therapeutic effect based on the silkworm *Staphylococcus aureus* infection model.
<Antibacterial Spectrum>

The antibacterial spectrum of the cyclic peptide compound shown by the foregoing formula (1) of the present invention can be investigated by MIC as mentioned before. As a result, it could be confirmed that, for example, each substance of the RH2180-5 Peak 5, Peak 6, and Peak 9 shows an antibacterial activity to gram-positive bacteria such as *Staphylococcus aureus* and *Enterococcus faecalis*, and in addition, exactly the same antibacterial activity as usual bacteria not only to MRSA but also to VRE, thereby showing that these are useful substances to many multiple-drug-resistant bacteria (see, Table 3 of Test Example 1 and Table 6 of Test Example 4).

Antibacterial spectra of the each peak substance, namely, antibacterial spectra of the cyclic peptide compounds shown by the foregoing formula (1) were investigated by MIC (Peak 1 Substance was not investigated) as to *Staphylococcus aureus* (MSSA 1) and *Enterococcus faecalis* (EF 1), which are the same kind of the chemical-sensitive bacteria as methicillin-resistant *Staphylococcus aureus* (MRSA 3 and MRSA 4) and vancomycin-resistant *Enterococcus* (VRE); and as a result, each peak substance showed almost the same MIC values between MSSA 1 and MRSA 3 and MRSA 4, and between EF 1 and VRE; and thus, it could be confirmed that a group of the compounds of the present invention is not influenced by chemical resistance including vancomycin resistance (see, Table 4 of Test Example 2).

The novel compound having a novel cyclic peptide structure shown by the above formula (1) of the present invention contains a compound showing an antibacterial activity to at least both methicillin-resistant *Staphylococcus aureus* (MRSA) and vancomycin-resistant *Enterococcus* (VRE).

Accordingly, it could be confirmed that the novel compound having a novel cyclic peptide structure of the present invention can be produced, for example, from a culture of the novel microorganism RH2180-5 (Accession No. NITE BP-870) and includes a novel compound showing an antibacterial activity to at least multiple-drug-resistant MRSA and VRE. Meanwhile, culturing method of the microorganism, purification method, and so forth, which were mentioned above, are mere examples that were selected to find the compounds of the present invention, so that it is natural to select different manufacturing methods in accordance with its purpose when there is a need to manufacture in a large scale with high efficiency, and so on.
<Therapeutic Drug for Infective Disease>

A therapeutic drug for an infective disease which contains the cyclic peptide compound shown by the above formula (1) or the pharmaceutically allowable salt thereof together with a pharmaceutically allowable carrier has an excellent therapeutic effect to an infective disease. It is recognized that especially some of the cyclic peptide compound shown by the above formula (1) or the pharmaceutically allowable salt thereof of the present invention have a higher therapeutic effect as compared with vancomycin not only in the silkworm *Staphylococcus aureus* infection model but also in the mouse *Staphylococcus aureus* infection model (this model will be explained later); and thus, they can be suitably used as an active ingredient of a therapeutic drug for an infective disease.

Content of the compound of the present invention in the foregoing therapeutic drug for an infective disease is not particularly restricted; and thus, the content thereof can be appropriately selected depending on its purpose and way of administration. In addition, a carrier, an excipient, and other additives which are used in formulation production of a usual antibiotic substance may be appropriately selected and used, to the degree not adversely affecting a pharmaceutical effect of the compound of the present invention, in accordance with requirement such as formulation.

Formulation of the therapeutic drug for an infective disease may be selected appropriately in accordance with an object and a method of administration; and thus, compounds of the present invention may be used for any oral administration such as powders, granules, capsule, tablets, and solution; or any parenteral administration such as injection, intravenous infusion, suppository, dermal administration, pernasality, enteral, and inhalant. As to excipients for oral administration, heretofore excipients such as lactose, glucose, starch, and polyvinyl pyrrolidone may be used; and when used as a solution, the compound of the present invention may be used in an inert solvent such as purified water and ethanol, together with pharmaceutically allowed emulsifier, suspending agent, solubilizer, sweetener, pH-controller, fragrance, preservative, and so forth.

When used as an injectable drug, a sterile aqueous solution such as a distilled water and a physiological saline solution for injection may be used, while in the case of a non-aqueous solution, illustrative example of the usable solution includes a vegetable oil such as an olive oil; and an alcohol such as ethanol, polyethylene glycol, and butylene glycol. Further, a tonicity agent, an emulsifier, a dispersing agent, a stabilizer, and a solubilizing agent such as cyclodextrin may be contained therein.

Dosage amount of product of the compound of the present invention which are formulated as mentioned above may be appropriately determined in accordance with symptom, age, gender, formulation, dosage route, frequency of administration per day, and so forth; but dosage amount for an adult is generally 10 to 1000 mg per day. However, for example, when it is used as intravenous drip infusion which is frequently used to cure a serious patient of a multiple-drug-resistant bacterium, there exists a possibility of needing more dosage amount.

EXAMPLES

Hereinafter, the present invention will be explained in more detail with reference to Examples, Test Examples, and Examination Examples; but the present invention is not limited to the concrete range of the following Examples and so on.

Example 1

<Isolation and Purification of the RH2180-5 Peak 5 Substance>
(1) Exploration of Microorganism Having Antibacterial Activity by MIC A soil taken from various places was suspended in a physiological saline solution, and then the supernatant thereof was applied on a GA medium and a HV medium; and after incubation at 30° C., grown bacteria was separated and then cultured in an YME medium, a SGM medium, or a CDY medium at 30° C. for 5 days. Equal amount of acetone was added thereinto; and after they were suspended and centrifugally separated, the resulting supernatant was evaporated. The residue thus resulted was diluted with a physiological saline solution, and then the antibacterial activity thereof to *Staphylococcus aureus* was evaluated by MIC with a broth microdilution method. As a result, antibacterial activity was found in culture supernatant of 3487 strains out of 14346 strains.
(2) Study of Microorganism Strain Capable of Producing Therapeutically Active Substance by Using the Silkworm *Staphylococcus Aureus* Infection Model (Hereinafter, this Model is Written as "Silkworm Model" for Short)

The therapeutic effects of 3487 the foregoing strains which showed an antibacterial activity were studied by using the silkworm model described in Patent Document 4; and as a result, the therapeutic effect was found in the culture supernatant of 45 strains.
(3) Purification of Therapeutically Active Substance by Referring to the Therapeutic Effect by Using the Silkworm Model Out of 45 strains mentioned above, a therapeutically active substance was purified from a culture supernatant of RH2180-5 which was separated from the soil taken from Okinawa. RH2180-5 was identified as a novel microorganism belonging to a genus *Lysobacter* by analysis of its 16S rRNA sequence, tendency of substances produced therefrom, and so forth, which will be mentioned later.

RH2180-5 was inoculated and cultured in 1200 mL of YME medium; and then, a method for purification of an antibiotic substance showing a therapeutic effect from a culture extract of 50% by mass acetone was investigated by referring to the therapeutic effect in the silkworm model. As a result, an antibiotic substance showing the therapeutic effect could be purified by dissolution to a butanol phase, water precipitation, chromatography by an ODS column, and RP-HPLC (reversed phase HPLC) by using an ODS column.

As shown in Table 2, specific activity of the therapeutic effect ($ED_{50}$) was raised by 300-folds relative to the acetone extract by the foregoing purification processes. On the other hand, the antibacterial activity (MIC) was raised only by 5-folds. This is presumably because the antibacterial activity shown in the acetone extract, the starting material of purification, was intervened with a substance other than the antibiotic substance showing the therapeutic effect in the finally purified product, and in addition, an antibacterial active substance other than the antibiotic substance showing the therapeutic effect could be removed by these selected purification processes.

Further, 9 compounds having a similar UV absorption pattern were detected in the foregoing RP-HPLC; and thus, it was confirmed that RH2180-5 produced at least 9 related compounds (see, UV absorption pattern of HPLC in FIG. 1).

Example 2

<Culturing of RH2180-5 and Manufacturing of the RH2180-5 Peak 5 Substance>

A microorganism taken from a slant culture of RH2180-5 by a platinum earpick was inoculated to a 500-mL Erlenmeyer flask filled with 100 mL YME medium, and then it was cultured by shaking at 30° C. for 3 days to obtain a seed culture. Then, 1.0 mL of this seed culture was inoculated to 12 500-mL Erlenmeyer flasks each filled with 100 mL of the said liquid medium; and then, they were shaken to culture at 30° C. for 5 days.

To the culture solution thus obtained was added equal amount of acetone; and then, after this mixture solution was thoroughly stirred and then centrifugally separated, the resulting supernatant was evaporated to remove acetone. Next, this material was subjected to dissolution to other solvent phase by using butanol. Dissolution to butanol solvent was done as following: the acetone extract was suspended into 80 mL of water, and after equal amount of butanol was added thereinto, the resulting mixture was thoroughly shaken and allowed to stand still. The resulting butanol layer was separated by a separation funnel, and then evaporated to dryness to be used for water precipitation. Water precipitation was done as following: after the foregoing dried residue was suspended into 80 mL of water, the resulting suspension was centrifugally separated to collect a deposited matter.

Sample of 75 mg butanol extract residue was dissolved into 60% methanol; and then by using 25 mL of Waters, Sep-Pak C18 (Sep-Pak is the registered trade mark, manufactured by Waters Corp.), elution was made with 60 to 100% methanol containing 0.1% of TFA by every 20 mL with 10% increment. As a result, the antibiotic-substance-containing fraction showing the therapeutic effect was eluted in the 70 to 80% methanol fraction.

These antibiotic-substance-containing fractions showing the therapeutic effect were collected and dried; and 22 mg weight was taken out from the sample thus obtained and dissolved into 50% methanol; and then by using the Senshu Pak SP-100 ODS column (diameter of 20 mm and length of 250 mm, manufactured by Senshu Scientific Co., Ltd.), elution was made with 75 to 95% methanol which contained 0.1% TFA. The antibiotic-substance-containing fraction showing the therapeutic effect was fractionated into 9 fractions which contained one compound in each fraction by the RP-HPLC with the above conditions.

From RP-HPLC as mentioned above, it was confirmed that the antibiotic-substance-containing fraction showing the therapeutic effect comprises a group of 9 compounds having a similar UV absorption pattern with a main component thereof being in the Peak 5 (UV instrument: Waters 2996 photo diode array) (see, FIG. 1).

By carrying out the above operations, 5.3 mg of the RH2180-5 Peak 5 Substance was obtained. With a manner similar to the above, each Peak substance was obtained from the respective peaks of Peak 1, Peak 2, Peak 3, Peak 4, Peak 6, Peak 7, Peak 8, and Peak 9.

Examination Example 1

<Structural Analysis of the RH2180-5 Peak 5 Substance>

An accurate mass spectrometry of the RH2180-5 Peak 5 Substance was made with a Bio TOF-Q mass spectrometer (manufactured by Bruker Daltonics, Inc.); and as a result, molecular weight thereof was found to be 1616.9 [(M+H)$^+$ of m/z=1617.8755 by ESI-TOF-MS].

Amino acid analysis was done by an amino acid analyzer (manufactured by Hitachi, Ltd.) after hydrolysis of the sample with 6N hydrochloric acid at 105° C.; and then, two molecules as to each of Thr, Glu, and Arg and one molecule as to each of Ser, Gly, and Ile were detected (FIG. 2).

Figure 9:
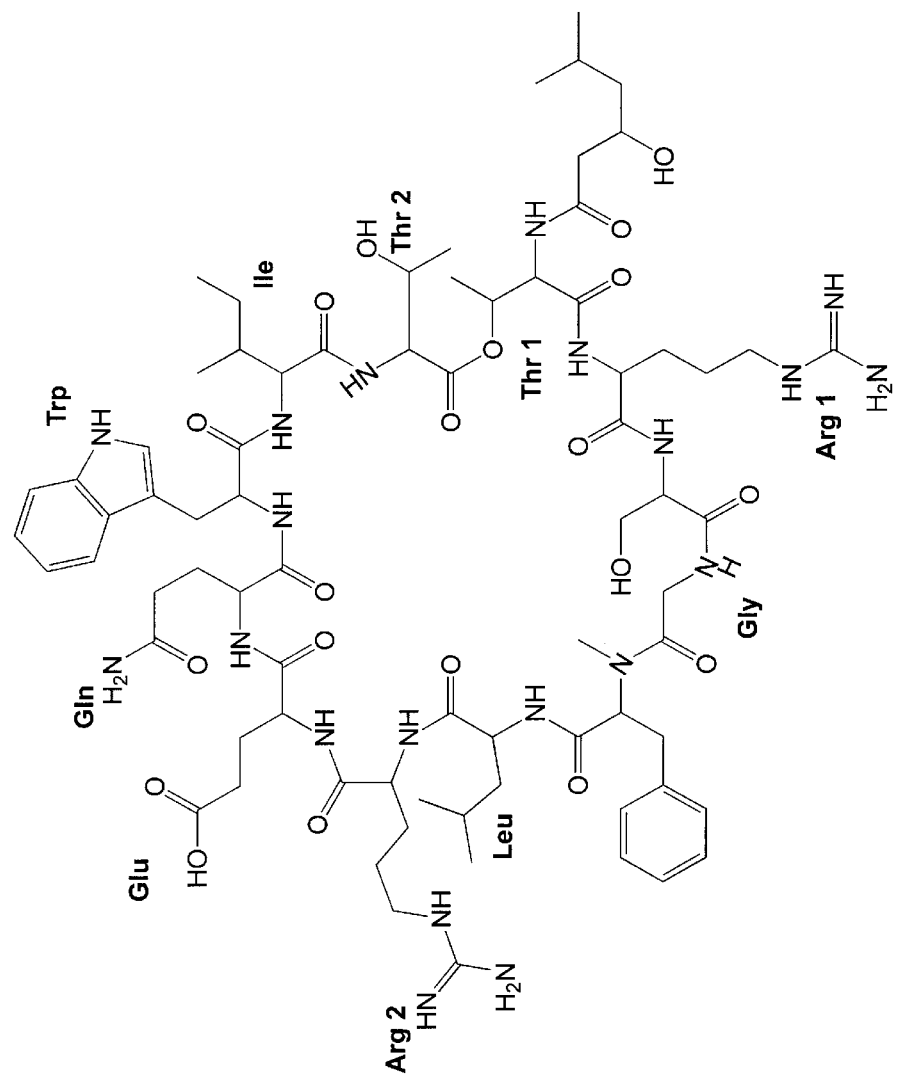
[FIG. 9]

Further, as a result of $^1$H-NMR and $^{13}$C-NMR analysis by ECA-500 NMR (manufactured by JEOL, Ltd,) (FIG. 3) and TOF-MS analysis (FIG. 4), the RH2180-5 Peak 5 Substance was identified as the cyclic peptide compound shown by the formula (1) whose R$^1$ is a 3-hydroxy-5-methyl-hexanoyl group, R$^2$ is a methyl group, and R$^3$ is an ethyl group, with the novel skeleton as shown in FIG. 9.

When the RH2180-5 Peak 5 Substance was acid-hydrolyzed and then analyzed as to D body or L body by a chiral column, it was found that Ile, Ser, Leu, and 2 Thrs (threonines) were L-bodies, while N-MePhe and two Args (arginines) and Trps (tryptophans) were D-bodies.

As to Gln and Glu, both of them are transformed to Glu by the acid hydrolysis, and then, they were detected as the 1:1 mixture of D-body and L-body. And thus, the peptide which contains glutamine and glutamic acid was reacted with bis(1, 1-trifluoroacetoxy) iodobenzene to transform glutamine to diaminobutyric acid; and then, after hydrolysis thereof, glutamic acid not reacted was analyzed for absolute configuration by a chiral column, whereby establishing that Gln was D-body and Glu was L-body. (Determination method of D-body and L-body by this decomposition method is a novel method used in this patent application for the first time.)

Absolute configuration R of the hydroxyl group of aliphatic acid chain was determined by modified Mosher method.

Figure 10:
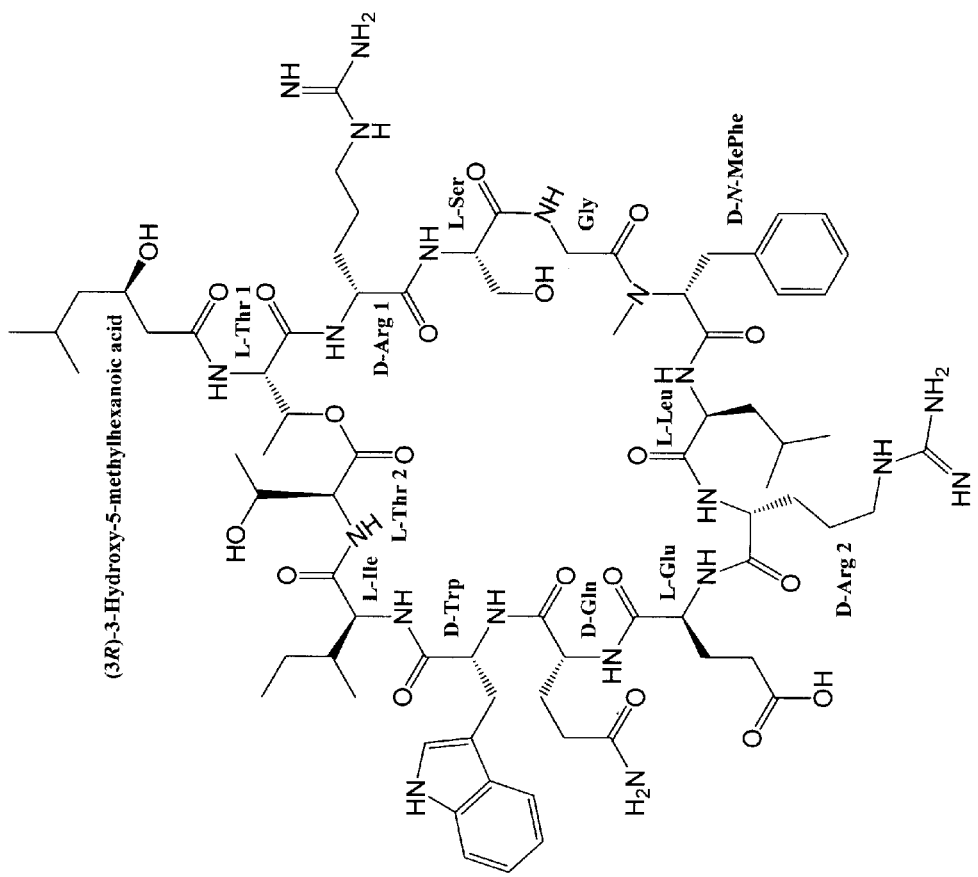
[FIG. 10]

As a result, it was found that the RH2180-5 Peak 5 Substance is a novel cyclic peptide compound with each amino acid thereof being in a three-dimensional conformation as shown in FIG. 10.

Examination Example 2

<Structural Analysis of the RH2180-5 Peak 9 Substance>

Figure 8:
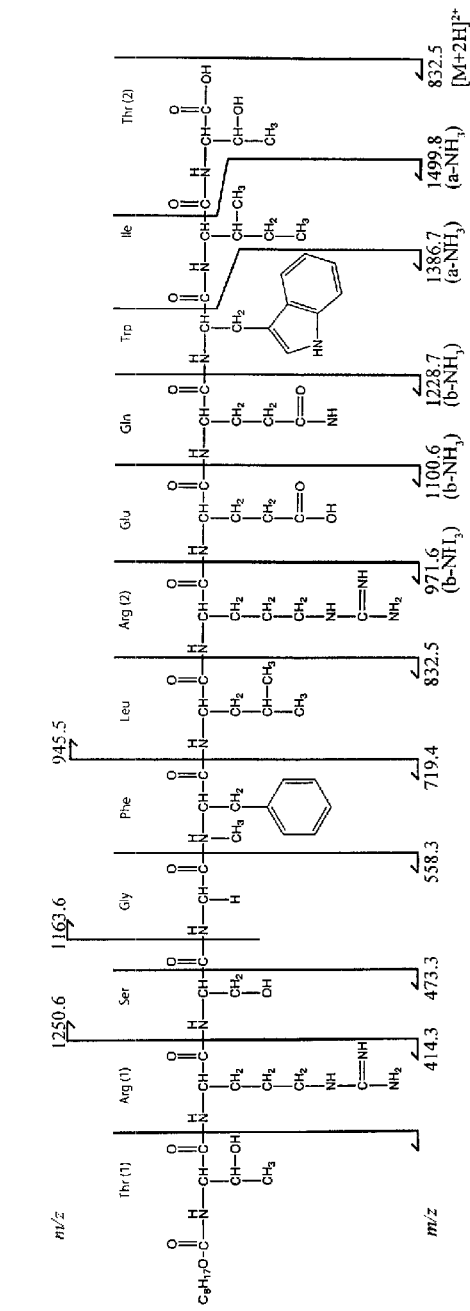
[FIG. 8]
Figure 8:
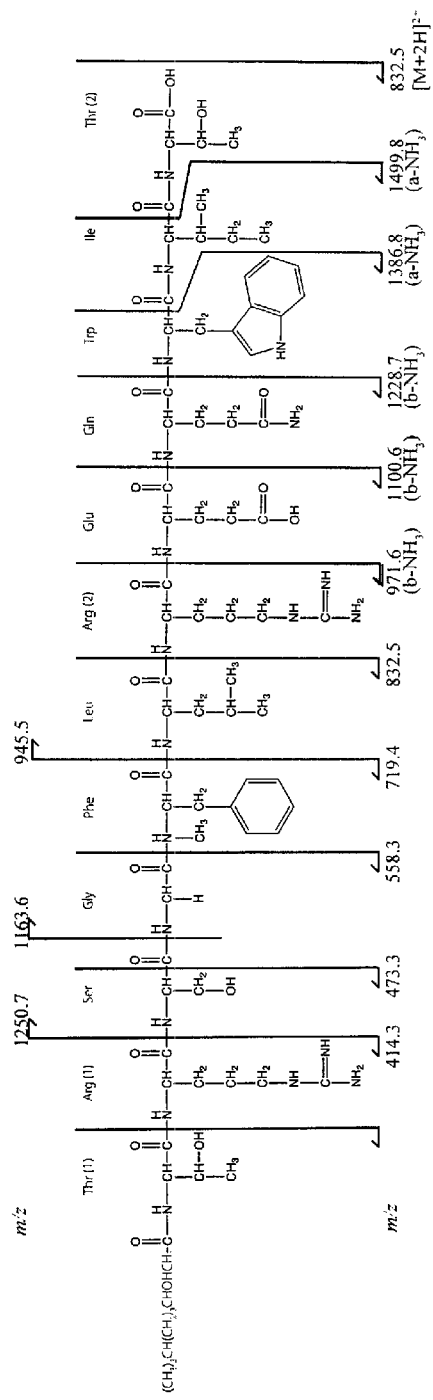

Structural analysis of the title compound was done with the structural analysis methods similar to those of Examination Example 1 except that the RH2180-5 Peak 9 Substance was used as the sample for the structural analysis (see, FIG. 8). As a result, it was confirmed that this substance is a cyclic peptide compound having the same chemical structure as that of the RH2180-5 Peak 5 Substance except that R$^1$ in the formula (1) is a 3-hydroxy-7-methyl-octanoyl group.

Further, the other peak substances were analyzed similarly, whereby confirming that they are the compounds having the same cyclic peptide structure as the RH2180-5 Peak 5 Substance and the RH2180-5 Peak 9 Substance in everything except that R$^1$, R$^2$, and R$^3$ are those shown in Table 1 (see, FIGS. 5, 6, 7, and 8).

Test Example 1

<Study of Antibacterial Spectra of Cyclic Peptide Compounds of the Present Invention>

Antibacterial spectrum of the RH2180-5 Peak 5 Substance to various bacteria including MRSA and VRE was studied. In addition, influence of chemical resistance was also studied. For study of the latter, Staphylococcus aureus and Enterococcus faecalis were selected, wherein measurement of MIC value of each peak substance was made by a broth microdilution method based on CLSI (formerly NCCLS: National Committee for Clinical Laboratory Standards) as to Staphylococcus aureus not showing resistance to a chemical (hereinafter abbreviated as "MSSA 1") and two kinds of MRSA showing resistance to many chemicals including methicillin (MRSA 3 and MRSA 4; see Table 3 for resistive chemicals) for Staphylococcus aureus; and as to Enterococcus faecalis not showing resistance to a chemical (hereinafter abbreviated as "EF 1") and showing resistance to vancomycin (hereinafter abbreviated as "VRE") for Enterococcus faecalis.

In addition, MIC values of the RH2180-5 Peak 6 Substance and the RH2180-5 Peak 9 Substance were measured as to MSSA 1 and EF 1 and their chemical resistant bacteria (MRSA 3, MRSA 4, and VRE). Various microorganisms used for the test and MIC measurement results thereof are shown in Table 3.

TABLE 3

| Strains | Resistance-showing chemicals | MIC (μg/mL) peak5 | peak6 | peak9 |
|---|---|---|---|---|
| Staphylococcus aureus (MSSA1) | Non | 5 | 5 | 5 |
| Staphylococcus aureus (MRSA3) | OX, FL, KM, TC, EM | 5 | 5 | 5 |
| Staphylococcus aureus (MRSA4) | OX, FL, KM, CP, CPLX | 5 | 5 | 5 |
| Enterococcus faecalis (EF1) | Non | 12.5 | 12.5 | 12.5 |
| Enterococcus faecalis (VRE) | VM | 12.5 | 12.5 | 12.5 |
| Enterococcus faecalis JCM5803 | | 25 | | |
| Bacillus subtilis JCM2499 | | 6.3 | | |
| Bacillus cereus JCM20037 | | 3.1 | | |
| Streptococcus pneumoniae | | 25 | | |
| Streptococcus agalactiae JCM5671 | | 100 | | |
| Streptococcus sanguinis JCM5708 | | 100 | | |
| Salmonella enteria | | >100 | | |
| Escherichia coli | | >100 | | |
| Serratia marcescens | | >100 | | |
| Pseudomonas aeruginosa | | >100 | | |
| Candida albicans | | >100 | | |

OX: oxacillin
FL: flomoxef
KM: kanamycin
TC: tetracycline
CP: chloramphenicol
EM: erythromycin
CPLX: ciprofloxacin
VM: vancomycin From the results shown in Table 3, it was confirmed that the RH2180-5 Peak 5 Substance shows an antibacterial activity to gram-positive bacteria because it shows an antibacterial activity to Staphylococcus aureus and Enterococcus faecalis. Further, it was confirmed that this is not influenced by multiple drug resistance including vancomycin because it shows the same MIC values to multiple-drug-resistant two MRSAs and VRE as the MIC value to usual bacteria (MSSA 1 and EF 1). These MIC values are not low and not so high in the antibacterial activity as compared with previously reported antibiotic substances; but as to the therapeutic effect, it was confirmed by the studies shown later that the therapeutic effect thereof is higher as compared with vancomycin.

In addition, it was confirmed that the RH2180-5 Peak 6 Substance and the RH2180-5 Peak 9 Substance show the same antibacterial activities to multiple-drug-resistant bacteria and to usual bacteria as those of the RH2180-5 Peak 5 Substance.

Test Example 2

<Comparative Study of the Antibacterial Activity of Each Peak Substance to Multiple-Drug-Resistant Bacteria and to Bacteria Not Having Chemical Resistance>

As to the novel peptide compounds of the present invention of 8 substances of the Peak 2 Substance to the Peak 9 Substance except for the Peak 1 Substance, which was in short of test amount, comparative study was made on the antibacterial activities to multiple-drug-resistant bacteria and to bacteria not having chemical resistance.

Test microorganisms of *Staphylococcus aureus* and *Enterococcus faecalis*, the same as Test Example 1, were selected; and measurement of MIC value of each peak substance was made by a broth microdilution method based on CLSI (formerly NCCLS: National Committee for Clinical Laboratory Standards) as to MSSA 1 and EF 1, and MRSA 3, MRSA 4, and VRE, the same as Test Example 1. These results are shown in Table 4.

TABLE 4

| Compounds | MSSA1 | MRSA3 | MRSA4 | EF1 | VRE |
|---|---|---|---|---|---|
| P1 | — | — | — | — | — |
| P2 | 12.5 | 12.5 | 6.3 | 50 | 50 |
| P3 | 25 | 25 | 25 | 50 | 50 |
| P4 | 12.5 | 25.0 | 12.5 | 50 | 25 |
| P5 | 6.3 | 6.3 | 6.3 | 12.5 | 12.5 |
| P6 | 6.3 | 6.3 | 3.1 | 50 | 25 |
| P7 | 12.5 | 12.5 | 12.5 | 50 | 25 |
| P8 | 12.5 | 12.5 | 12.5 | 50 | 25 |
| P9 | 6.3 | 6.3 | 6.3 | 12.5 | 12.5 |

MIC (μg/mL)
MSSA1: *Staphylococcus aureus*
MRSA3: *Staphylococcus aureus* resistant to OX, FL, KM, TC, and EM
MRSA4: *Staphylococcus aureus* resistant to OX, FL, KM, CP, and CPLX
EF1: *Enterococcus faecalis*
VRE: Vancomycin-resistant *Enterococcus*
OX: oxacillin
FL: flomoxef
KM: kanamycin
TC: tetracycline
CP: chloramphenicol
EM: erythromycin
CPLX: ciprofloxacin As a result, the MIC value itself of each peak substance is larger as compared with previously reported antibacterial agents; but when comparison is made between usual bacteria and multiple-drug-resistant bacteria thereof (between MSSA 1 and MRSA 3 and MRSA 4, and between EF 1 and VRE), MIC values are almost same, whereby confirming that antibacterial activity of each peak substance is not influenced by the multiple drug resistance.

Meanwhile, in the case of the cyclic peptide compound of the present invention, it is confirmed that the antibacterial activity does not necessarily coincide with the therapeutic effect. For example, the RH2180-5 Peak 5 Substance which shows, as the MIC values to MSSA, 6.3 μg/mL in Table 4 and 5 μg/mL in Table 3; but as a study result of the therapeutic effect to the mouse *Staphylococcus aureus* infection model ($ED_{50}$), which will be mentioned later, $ED_{50}$ value thereof is about one third of vancomycin, whereby confirming high therapeutic effect.

Even though MIC values of 5 μg/mL and 6 μg/mL are in the level of MIC value shown by the resistant bacteria in vancomycin, the cyclic peptide compound of the present invention shows adequate therapeutic effect; and one reason for this may be because compounds of the present invention express the antibacterial activity by an action mechanism different from that of existing drugs, which probably reflects to the therapeutic effect. If the antibacterial activity is expressed by an action mechanism different from that of existing drugs, separation frequency of resistant strain is expected to be low at least at this moment, so that this may be regarded as an advantageous aspect of the cyclic peptide compound of the present invention.

Test Example 3

<Study of Therapeutic Effect and Toxicity of the RH2180-5 Peak 5 Substance in the Mouse *Staphylococcus Aureus* Infection Model (Hereinafter, this Model is Written as "Mouse Model" for Short)>

Smith strain of *Staphylococcus aureus* was suspended in 7% mucin+0.2 mM ferric ammonium citrate, and $6.2 \times 10^6$ ($20 \times LD50$) thereof was administered into the peritoneal cavity of 5 mice per group (ICR female of four weeks of age). Each drug was injected hypodermically 2 hours after administration of the bacterium by the method shown below.

To this mouse model was injected hypodermically the RH2180-5 Peak 5 Substance dissolved in PBS in such a manner that amount thereof may become 25 mg/kg, 12.5 mg/kg, and 6.3 mg/kg; and then the therapeutic effect ($ED_{50}$) thereof was studied by measuring the survival umbers one day after the administration (5 mice per group). Similarly, $ED_{50}$ of vancomycin to the mouse model used this time was studied. In the case of the RH2180-5 Peak 5 Substance, survival of totality of mice was confirmed with administration of 25 mg/kg under the condition of no survival with PBS administration. Here, $ED_{50}$ values were obtained by the probit method.

The obtained results are shown in Table 5. The RH2180-5 Peak 5 Substance shows the therapeutic effect to the mouse model with $ED_{50}$ value of 0.6 mg/kg, which is clearly lower than $ED_{50}$ of the simultaneously studied vancomycin (1.6 mg/kg), thereby confirming that an antibiotic substance having high therapeutic effect to *Staphylococcus aureus* is produced.

TABLE 5

Therapeutic effect in the mouse *Staphylococcus aureus* infection model

| Sample | $ED_{50}$ (mg/Kg) |
|---|---|
| RH2180-5 peak5 | 0.6 |
| Vancomycin | 1.6 |

Each drug was injected hypodermically two hours after $6.2 \times 10^6$ ($20 \times LD_{50}$) of *S. aureus* Smith strain was administered into the peritoneal cavity of a mouse (ICR female of four weeks of age).

Further, the RH2180-5 Peak 5 Substance was injected hypodermically to the mouse to study acute toxicity of the RH2180-5 Peak 5 Substance to the mouse by observation one day after the administration. In acute toxicity, there was no toxicity observed (mouse was not killed) till administration amount of 50 mg/kg, which corresponds to 80-folds of $ED_{50}$, the highest concentration among the study; and thus, it was suggested that the RH2180-5 Peak 5 Substance is low in toxicity.

From the above results, it could be confirmed that the antibiotic RH2180-5 Peak 5 Substance (P5) of the present invention produced from RH2180-5 shows excellent $ED_{50}$ value to *Staphylococcus aureus* as compared with vancomycin, whereby showing high therapeutic effect; and in addition, from the study results of the antibacterial activity by MIC, it could be confirmed that the substance has excellent characteristics of showing effectiveness not only to MRSA, which is highly problematic clinically, but also to VRE, which is expected to become problematic similarly to MRSA from now on.

Further, 8 out of 9 novel compounds having basic skeleton of the novel peptide structure of the present invention which were isolated and purified from a culture of RH2180-5 (antibacterial spectrum of the Peak 1 substance was not studied) showed almost the same MIC values to the multiple-drug resistant strains and to the strains not acquired similar multiple-drug resistant properties (Table 4), so that it could be confirmed that the novel compounds having basic skeleton of the novel peptide structure of the present invention can be used as an anti-infective therapeutic drug effective especially to multiple-drug-resistant bacteria.

Test Example 4

<Study of Antibacterial Spectrum of the RH2180-5 Peak 5 Substance>

Antibacterial spectrum of the foregoing RH2180-5 Peak 5 Substance to various microorganisms including MRSA and VRE was studied. Each MIC value for the case added with 10% blood serum and for the case not added with the same was measured by a broth microdilution method based on CLSI (formerly NCCLS: National Committee for Clinical Laboratory Standards). The results thereof are shown in Table 6.

TABLE 6

| | MIC (µg/ml) | |
|---|---|---|
| Microorganisms | Without serum | With 10% serum |
| Methicillin susceptible *S. aureus* MSSA1 (clinical isolate) | 3.1 | 1.5 |
| Methicillin resistant *S. aureus* MRSA3 (clinical isolate) | 12.5 | 1.5 |
| Methicillin resistant *S. aureus* MRSA4 (clinical isolate) | 12.5 | 1.5 |
| *Staphylococcus aureus* Smith ATCC 13709 | 6.25 | 1.5 |
| *Enterococcus faecalis* EF1 | 12.5 | 6.3 |
| Vancomycin-resistant *Enterococcus faecalis* EF5 | 12.5 | 6.3 |
| *Enterococcus faecalis* JCM5803 | 25 | ND |
| *Bacillus subtilis* JCM2499 | 6.3 | 1.5 |
| *Bacillus cereus* JCM20037 | 3.1 | 0.8 |
| *Listeria monocytogenes* | ND | 6.3 |
| *Streptococcus pneumoniae* | ND | 25 |
| *Streptococcus sanguinis* JCM5678 | ND | 100 |
| *Streptococcus agalactiae* JCM5671 | ND | 100 |
| *Streptococcus pyogenes* | ND | 50 |
| *Mycobacterium fortuitum* | 7.8 | 3.9 |
| *Mycobacterium smegmatis* | 7.8 | 15.6 |
| *Serratia marcescens* (clinical isolate) | >100 | >50 |
| *Escherichia coli* W3110 | >100 | >100 |
| *Pseudomonas aeruginosa* PAO1 | >100 | >50 |
| *Salmonella enterica* | >100 | ND |
| *Candida albicans* ATCC10231 | >100 | >100 |
| *Candida tropicalis* pK233 | >100 | >100 |
| *Cryptococcus neoformans* H99 | >100 | >100 |

ND: Not determined

From the results in Table 6, it could be confirmed that the RH2180-5 Peak 5 Substance is effective to gram-positive bacteria and increases its activity by addition of blood serum.

Test Example 5

<Study of Antibacterial Activity of the RH2180-5 Peak 5 Substance>

To CA-Mueller Hinton Broth medium were taken $1.8 \times 10^8$ *Staphylococcus aureus*, and then the foregoing RH2180-5 Peak 5 Substance (25 µg/mL), vancomycin (VM, 5 µg/mL), and gentamicin (GM, 2.5 µg/mL) were added thereinto; and then, survived cell numbers after 15 minutes, 30 minutes, 60 minutes, and 120 minutes were obtained as CFU (colony forming unit/mL). The results thereof are shown in Table 7.

TABLE 7

| | CFU/ml of *S. aureus* | | | |
|---|---|---|---|---|
| Time (minutes) | RH2180-5 Peak 5 Substance (25 µg/ml) | VM (5 µg/ml) | GM (2.5 µg/ml) | Control (no drug) |
| 0 | | | | $1.8 \times 10^8$ |
| 15 | $<1 \times 10^4$ | $8.5 \times 10^7$ | $2.6 \times 10^7$ | |
| 30 | $<1 \times 10^4$ | $4.9 \times 10^7$ | $7.6 \times 10^5$ | |
| 60 | $<1 \times 10^4$ | $6.8 \times 10^7$ | $1.6 \times 10^5$ | |
| 120 | $<1 \times 10^4$ | $3.4 \times 10^7$ | $4.0 \times 10^5$ | |

*VM: Vancomycin;
GM: Gentamicin

From the results in Table 7, it could be confirmed that number of *Staphylococcus aureus* was decreased immediately after addition of the RH2180-5 Peak 5 Substance as compared with addition of vancomycin and gentamicin.

In addition, it was found from this result and so forth that the antibiotic-substance-containing fraction obtained by fractionation of a culture which is produced by culturing of the microorganism with Accession No. NITE BP-870, and in addition, a microbial protection agent which contains the antibiotic substance obtained from the culture thereof are useful. It was found that not only a microbial protection agent which contains the RH2180-5 Peak 5 Substance is useful but also a microbial protection agent which contains even other peak substances or the fraction before isolation of a substance as the substance are similarly useful.

Test Example 6

<Study of Bacteriolytic Activity of the RH2180-5 Peak 5 Substance>

*Staphylococcus aureus* was diluted in CA-Mueller Hinton Broth medium; and then, the RH2180-5 Peak 5 Substance, vancomycin, and daptomycin were added thereinto with the concentrations thereof being five times as much as those of Test Example 1; and then, the microorganism was cultured at 37° C. By using an absorption spectrometer (manufactured by Shimadzu Corp.), absorbance at 600 nm ($OD_{600}$) after their addition was followed with passage of time. The results thereof are shown in FIG. 11.

Figure 11:
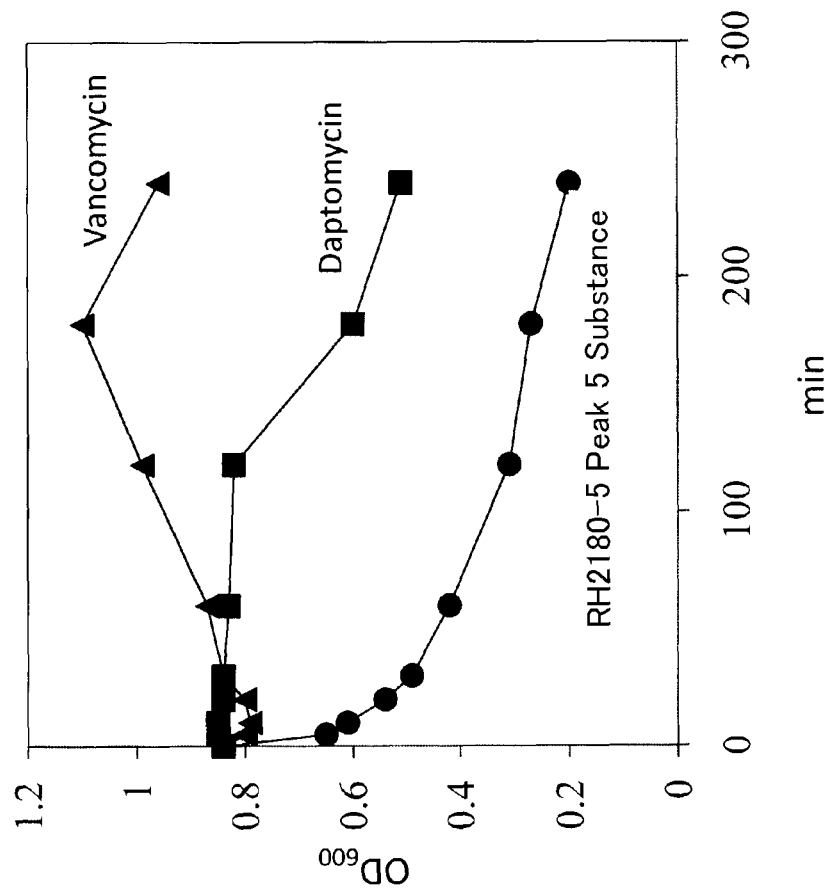
[FIG. 11]

From the results of FIG. 11, it could be confirmed that the RH2180-5 Peak 5 Substance shows the bacteriolytic activity because decrease of absorbance ($OD_{600}$) thereof is larger as compared with vancomycin and daptomycin.

Example 3

<Formulation Production of the RH2180-5 Peak 5 Substance>

<<Tablet Formulation>>

After 20.0 mg of the RH2180-5 Peak 5 Substance, 40 mg of lactose, 20 mg of starch, and 5 mg of low-degree substituted hydroxypropyl cellulose were uniformly mixed, granules for tablets were prepared by a wet granulation method by using 8% by mass of aqueous solution of hydroxypropyl cellulose as a binding material. To this was added 0.5 to 1 mg of magnesium stearate, amount necessary to afford sliding properties to the granules, and then they were tableted by a tableting machine.

<<Solution Formulation>>

Injection solution was prepared by dissolving 10.0 mg of the RH2180-5 Peak 5 Substance into 10 mL of 2% by mass of aqueous solution of 2-hydroxypropyl-β-cyclodextrin.

Examination Example 3

<Analysis of 16S rRNA>

Bases of 16S rRNA of RH2180-5 was amplified by a colony PCR method; and then, the amplified RNA fragments were analyzed by a sequencer. As a result, base sequence corresponding to almost entire length of the 16S rRNA region shown in the Sequence No. 1, except for some bases at the 5' terminal side and the 3' terminal side, was determined. Then, homology search with an existing strain belonging to a genus Lysobacter was executed by using NCBI BLAST relative to this base sequence. As a result, RH2180-5 showed homology rate of 99% relative to the existing Lysobacter enzymogenes DSM 2043T strain; and thus, it was considered that RH2180-5 is a microorganism belonging to a genus Lysobacter.

<With Regard to Novelty of RH2180-5>

RH2180-5 has many similarities in chemical properties to the Lysobacter enzymogenes DSM 2043T strain; but the antibacterial spectra of the produced physiologically active substances are different. In addition, compounds which are a main body of the physiologically active substances are "the RH2180-5 Peak 5 Substance and its related compounds which have a useful pharmaceutical function" having a basic skeleton of the novel cyclic peptide structure not reported before; and thus, they are completely different in this point. This poses a significant difference with the existing strain. Accordingly, in view of the above results, RH2180-5 was judged to be a novel microorganism belonging to a genus Lysobacter.

Industrial Applicability

The novel cyclic peptide compound of the present invention shows effectiveness to multiple-drug-resistant bacteria such as MRSA and VRE, which became a serious clinical problem; and thus, this can be used as a new therapeutic drug for an infective disease. In addition, the novel microorganism strain of the present invention can be used suitably to manufacture the foregoing novel, useful cyclic peptide compound.

Further, the present invention has an industrial applicability to provide a novel antibiotic-substance-containing fraction, an antibiotic substance contained therein, and a method for manufacturing the said antibiotic-substance-containing fraction and a novel, useful antibiotic substance obtained therefrom.

The present application is based on the Japanese Patent Application No. 2010-119138, the Japanese Patent Application No. 2010-119139, and the Japanese Patent Application No. 2010-119140 which were filed on May 25, 2010 as the Japanese application patents; and totality of the contents in these applications are recited hereinto and incorporated as the specification disclosure of the present applied invention.

Accession No.

NITE BP-870

Sequence Chart Free Text

Sequence chart No. 1 shows the base sequence of almost entire length of 16S rRNA of an unknown strain belonging to genus Lysobacter.

---

The invention claimed is:

1. A cyclic peptide compound shown by the following formula (1) or a pharmaceutically allowable salt thereof:

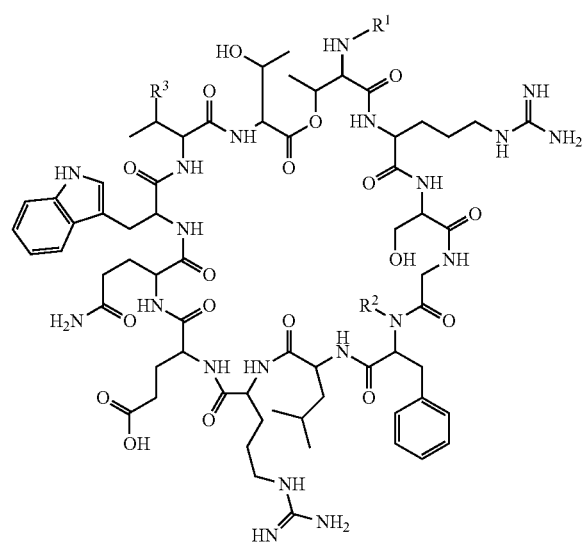

Formula (1)

wherein, in the formula (1), $R^1$ represents an acyl group having 7, 8, or 9 carbon atoms and optionally containing a substituent group; $R^2$ represents a methyl group or a hydrogen atom; and $R^3$ represents an ethyl group or a methyl group.

2. The cyclic peptide compound or the pharmaceutically allowable salt thereof according to claim 1, wherein the substituent group of $R^1$ in the above formula (1) is a hydroxyl group.

3. The cyclic peptide compound or the pharmaceutically allowable salt thereof according to claim 1, wherein $R^1$ in the above formula (1) is a 3-hydroxy-5-methyl-hexanoyl group, a 3-hydroxy-6-methyl-heptanoyl group, or a 3-hydroxy-7-methyl-octanoyl group.

4. The cyclic peptide compound or the pharmaceutically allowable salt thereof according to claim 1, wherein, in the above formula (1), $R^1$ is a 3-hydroxy-5-methyl-hexanoyl group, $R^2$ is a methyl group, and $R^3$ is an ethyl group.

5. The cyclic peptide compound or the pharmaceutically allowable salt thereof according to claim 1, wherein, in the above formula (1), $R^1$ is a 3-hydroxy-7-methyl-octanoyl group, $R^2$ is a methyl group, and $R^3$ is an ethyl group.

6. The cyclic peptide compound or the pharmaceutically allowable salt thereof according to claim 1, wherein the cyclic peptide compound or the pharmaceutically allowable salt thereof is obtained from a culture that is produced by culturing of RH2180-5strain, which belongs to a genus *Lysobacter* with Accession No. NITE BP-870 in NITE Patent Microorganisms Depositary (NPMD) of Incorporated Administrative Agency National Institute of Technology and Evaluation (NITE), or its mutant strain capable of producing a compound similar to the compound produced from the foregoing strain.

7. A method for manufacturing a cyclic peptide compound or the pharmaceutically allowable salt thereof, comprising:
cultring the RH2180-5strain, which is capable of producing the cyclic peptide compound according to claim 1 and belongs to a genus *Lysobacter* with Accession No. NITE BP-870 in NITE Patent Microorganisms Depositary (NPMD) of Incorporated Administrative Agency National Institute of Technology and Evaluation (NITE), or its mutant strain capable of producing a compound similar to the compound produced from the foregoing strain.

8. A therapeutic drug for an infective disease, comprising:
the cyclic peptide compound or the pharmaceutically allowable salt thereof according to claim 1, and
a pharmaceutically allowable carrier.

9. An antibiotic-substance-containing fraction, comprising:
the cyclic peptide compound or the pharmaceutically allowable salt thereof according to claim 1,
wherein the antibiotic-substance-containing fraction is obtained by fractionating a culture which is produced by culturings *Lysobacter* with Accession No. NITE BP-870.

10. The antibiotic-substance-containing fraction according to claim 9, wherein the antibiotic-substance-containing fraction is a fraction which comprises an antibiotic substance showing an antibacterial activity.

11. The antibiotic-substance-containing fraction according to claim 9, wherein the antibiotic-substance-containing fraction shows an antibacterial activity at least to both methicillin-resistant *Staphylococcus aureus* (MRSA) and vancomycin-resistant *Enterococcus* (VRE).

12. The antibiotic-substance-containing fraction according to claim 9, wherein the antibiotic-substance-containing fraction is a fraction which comprises an antibiotic substance showing a therapeutic effect to an infective disease at least due to *Staphylococcus aureus*.

13. The antibiotic-substance-containing fraction according to claim 12, wherein the antibiotic-substance-containing fraction comprises an antibiotic substance showing a therapeutic effect to an infective disease at least due to *Staphylococcus aureus*with the therapeutic effect thereof being the same or higher as compared with vancomycin.

14. The antibiotic-substance-containing fraction according to claim 9, wherein the antibiotic-substance-containing fraction comprises an antibiotic substance showing an antibacterial activity but not substantially showing a therapeutic effect.

15. The antibiotic-substance-containing fraction according to claim 14, wherein the antibiotic substance showing an antibacterial activity but not substantially showing a therapeutic effect is adapted to be used as a microbial protection agent.

16. A method for manufacturing an antibiotic substance, comprising:
culturing a microorganism belonging to a genus *Lysobacter* with Accession No. NITE BP-870 in a culture, and
separating and purifying at least one of an antibiotic substance showing an antibacterial activity and an antibiotic substance showing a therapeutic effect to an infective disease from the culture,
wherein the antibiotic substance comprises the cyclic peptide compound or the pharmaceutically allowable salt thereof according to claim 1.

17. The method for manufacturing an antibiotic substance according to claim 16, wherein the antibiotic substance shows an antibacterial activity at least to both methicillin-resistant *Staphylococcus aureus* (MRSA) and vancomycin-resistant *Enterococcus* (VRE).

18. The method for manufacturing an antibiotic substance according to claim 16, wherein the antibiotic substance shows a therapeutic effect to an infective disease at least due to *Staphylococcus aureus*.

19. The method for manufacturing an antibiotic substance according to claim 16, wherein the antibiotic substance is an antibiotic substance showing an antibacterial activity but not substantially showing a therapeutic effect.

20. An antibiotic substance, comprising:
the cyclic peptide compound or the pharmaceutically allowable salt thereof according to claim 1,
wherein the antibiotic substance is obtained from a culture which is produced by culturing a microorganism belonging to a genus *Lysobacter* with Accession No. NITE BP-870.

21. The antibiotic substance according to claim 20, wherein the antibiotic substance shows an antibacterial activity at least to both methicillin-resistant *Staphylococcus aureus*(MRSA) and vancomycin-resistant *Enterococcus* (VRE).

22. The antibiotic substance according to claim 20, wherein the antibiotic substance shows a therapeutic effect to an infective disease at least due to *Staphylococcus aureus*.

23. The antibiotic substance according to claim 22, wherein the antibiotic substance shows a therapeutic effect to an infective disease at least due to *Staphylococcus aureus* with the therapeutic effect thereof being the same or higher as compared with vancomycin.

24. An antibiotic substance, comprising:
the cyclic peptide compound or the pharmaceutically allowable salt thereof according to claim 1,
wherein the antibiotic substance shows an antibacterial activity at least to both methicillin-resistant *Staphylococcus aureus* (MRSA) and vancomycin-resistant *Enterococcus*(VRE) while showing a therapeutic effect to an infective disease at least due to *Staphylococcus aureus*, and
wherein the antibiotic substance is obtained from a culture which is produced by culturing a microorganism belonging to a genus *Lysobacter* with Accession No. NITE BP-870.

25. The antibiotic substance according to 20, wherein the antibiotic substance is shown by the following formula (1):

Formula (1)

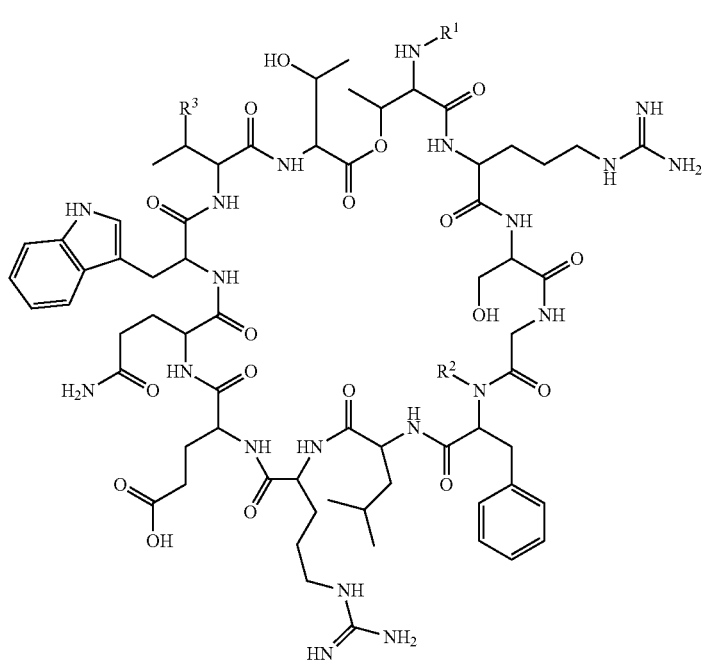

wherein, in the formula (1), $R^1$ represents an acyl group having 7, 8, or 9 carbon atoms and optionally containing a substituent group; $R^2$ represents a methyl group or a hydrogen atom; and $R^3$ represents an ethyl group or a methyl group.

26. A microbial protection agent, comprising:
the antibiotic-substance-containing fraction according to claim 9.

27. A microbial protection agent, comprising:
the antibiotic substance according to claim 20.

* * * * *